(12) United States Patent
Kim et al.

(10) Patent No.: US 11,911,153 B2
(45) Date of Patent: Feb. 27, 2024

(54) DEVICE FOR MEASURING BIOLOGICAL INFORMATION INCLUDING SENSOR ARRAY AND METHOD OF MEASURING BIOLOGICAL INFORMATION USING DEVICE

(71) Applicants: UNIVERSITY-INDUSTRY COOPERATION GROUP OF KYUNG HEE UNIVERSITY, Yongin-si (KR); Korea Electronics Technology Institute, Seongnam-si (KR)

(72) Inventors: Sun Kook Kim, Yongin-si (KR); Sung Ho Lee, Seoul (KR); Min Goo Lee, Seoul (KR); Hyuk Sang Jung, Seoul (KR); Min Jung Kim, Hwaseong-si (KR); Young Ki Hong, Seoul (KR); Won Geun Song, Gunpo-si (KR)

(73) Assignees: UNIVERSITY-INDUSTRY COOPERATION GROUP OF KYUNG HEE UNIVERSITY, Yongin-si (KR); Korea Electronics Technology Institute, Seongnam-si (KR)

( * ) Notice: Subject to any disclaimer, the term of this patent is extended or adjusted under 35 U.S.C. 154(b) by 711 days.

(21) Appl. No.: 17/089,273

(22) Filed: Nov. 4, 2020

(65) Prior Publication Data

US 2021/0068718 A1 Mar. 11, 2021

Related U.S. Application Data

(62) Division of application No. 15/777,057, filed as application No. PCT/KR2016/000160 on Jan. 8, 2016, now Pat. No. 11,129,555.

(30) Foreign Application Priority Data

Nov. 17, 2015 (KR) .................. 10-2015-0160779
Nov. 27, 2015 (KR) .................. 10-2015-0167207

(Continued)

(51) Int. Cl.
*G01K 13/20* (2021.01)
*G01K 15/00* (2006.01)
(Continued)

(52) U.S. Cl.
CPC .............. *A61B 5/1455* (2013.01); *A61B 5/01* (2013.01); *A61B 5/02055* (2013.01);
(Continued)

(58) Field of Classification Search
CPC ............ G01K 7/16; G01K 7/18; G01K 7/183; G01K 7/186; G01K 7/20; G01K 7/203;
(Continued)

(56) References Cited

U.S. PATENT DOCUMENTS

| 6,180,867 | B1* | 1/2001 | Hedengren | G01K 7/02 |
| | | | | 374/E7.004 |
| 2016/0161343 | A1* | 6/2016 | Smith | G01K 7/16 |
| | | | | 374/185 |
| 2019/0110692 | A1* | 4/2019 | Pardey | A61B 5/7225 |

FOREIGN PATENT DOCUMENTS

| CN | 102198004 A | 9/2011 |
| CN | 102694510 A | 9/2012 |

(Continued)

OTHER PUBLICATIONS

Communication dated Jul. 13, 2020, issued by the Chinese Patent Office in counterpart Chinese Application No. 201680079251.0.
(Continued)

*Primary Examiner* — Herbert K Roberts
(74) *Attorney, Agent, or Firm* — Sughrue Mion, PLLC

(57) ABSTRACT

The present invention provides a device for measuring biological information including a sensor array, wherein the sensor array includes a plurality of sensors that are either sensors for amplifying photoreactivity or sensors forming an island network connected by a plurality of multi-channels
(Continued)

and, in the device, the average value of biological information about the skin tissues is measured based on values output from the sensor array, and a method of measuring biological information using the device.

12 Claims, 31 Drawing Sheets

(30) Foreign Application Priority Data

Dec. 16, 2015 (KR) ........................ 10-2015-0180337
Dec. 24, 2015 (KR) ........................ 10-2015-0186407

(51) Int. Cl.
    *A61B 5/01*         (2006.01)
    *A61B 5/1455*     (2006.01)
    *A61B 5/0205*     (2006.01)
    *A61B 5/024*      (2006.01)
    *A61B 5/00*       (2006.01)

(52) U.S. Cl.
    CPC ...... *A61B 5/02438* (2013.01); *A61B 5/02444* (2013.01); *A61B 5/6833* (2013.01); *G01K 13/20* (2021.01); *G01K 15/005* (2013.01); *A61B 2560/0238* (2013.01); *A61B 2560/0412* (2013.01); *A61B 2562/0271* (2013.01); *A61B 2562/066* (2013.01)

(58) Field of Classification Search
    CPC ............ G01K 7/206; G01K 7/21; G01K 7/22; G01K 7/223; G01K 7/226; G01K 7/24; G01K 7/245; G01K 7/25; G01K 2213/00; A61B 5/01; A61B 5/015; A61B 5/02055; A61B 5/6801; A61B 5/683; A61B 5/6832; A61B 5/6833; A61B 5/68335; A61B 2018/00791; A61B 2018/00797; A61B 2018/00815; A61B 2018/00875; A61B 2562/0271; A61B 2562/066

See application file for complete search history.

(56) References Cited

FOREIGN PATENT DOCUMENTS

| | | | |
|---|---|---|---|
| CN | 103035734 | A | 4/2013 |
| CN | 103681957 | A | 3/2014 |
| CN | 104903732 | A | 9/2015 |
| JP | 2001-008902 | A | 1/2001 |
| JP | 2004-000138 | A | 1/2004 |
| JP | 2005-103054 | A | 4/2005 |
| KR | 10-2005-0043702 | A | 5/2005 |
| KR | 10-2006-0048641 | A | 5/2006 |
| KR | 10-1133082 | B1 | 4/2012 |
| KR | 20120121852 | A * | 11/2012 |
| KR | 10-2014-0037702 | A | 3/2014 |
| KR | 10-2014-0119795 | A | 10/2014 |
| KR | 10-2015-0068333 | A | 6/2015 |
| WO | 2013114293 | A1 | 8/2013 |

OTHER PUBLICATIONS

Korean Office Action for KR 10-2015-0180337 dated Aug. 17, 2017.
Korean Office Action for KR 10-2015-0160779 dated Jun. 20, 2017.
International Search Report for PCT/KR2016/000160 dated Aug. 16, 2016.
Communication dated Jan. 14, 2021, issued by the Chinese Patent Office in counterpart Chinese Application No. 201680079251.0.

* cited by examiner

SENSOR
170

SWITCHING
THIN FILM TRANSISTOR
160

DEVICE FOR MEASURING BIOLOGICAL INFORMATION INCLUDING SENSOR ARRAY AND METHOD OF MEASURING BIOLOGICAL INFORMATION USING DEVICE

CROSS-REFERENCE TO RELATED APPLICATION

This application is a Divisional Application of U.S. application Ser. No. 15/777,057, filed on May 17, 2018, which is a National Stage Entry of PCT/KR2016/000160, filed on Jan. 8, 2016, which claims the priority benefit of Korean Patent Application No. 10-2015-0160779, filed on Nov. 17, 2015, Korean Patent Application No. 10-2015-0167207, filed on Nov. 27, 2015, Korean Patent Application No. 10-2015-0180337, filed on Dec. 16, 2015, and Korean Patent Application No. 10-2015-0186407, filed on Dec. 24, 2015, in the Korean Intellectual Property Office. Each of the above applications is hereby expressly incorporated by reference, in its entirety, into the present application.

BACKGROUND OF THE DISCLOSURE

Field of the Disclosure

The present invention relates to a device for measuring biological information including a sensor array and a method of measuring biological information using the device. More particularly, the present invention relates to a device for measuring biological information including a sensor array, wherein the sensor array includes a plurality of sensors that are either sensors for amplifying photoreactivity or sensors forming an island network connected by a plurality of multi-channels and, in the device, the average value of biological information about the skin tissues is measured based on values output from the sensor array, and to a method of measuring biological information using the device.

Description of the Related Art

The body has a protective mechanism to protect itself against heat or cold. Flexible multi-measurement sensors have been required to prevent or treat body temperature-related diseases, such as thermal fatigue, heat stroke, and hypothermia, that are caused by various factors inhibiting the protective mechanism.

However, most conventional multi-measurement sensors include a plurality of sensors for acquiring various biological information as well as a pulse oximeter for measuring temperature, oxygen saturation, and heart rate of an object (e.g., skin surface of the body). Thus, the conventional multi-measurement sensors have limitations in accurately measuring biological information (at least one of temperature, oxygen saturation, and heart rate) of the object. Also, in the case of the conventional multi-measurement sensors, since the biological information of an object is mainly measured using only a single sensor, only biological information included in a certain area of the object corresponding to the area of the single sensor may be measured. Accordingly, there are problems that the accuracy of biological information may be influenced by the position of a sensor attached to an object or the size of the sensor, and biological information may not be accurately measured to the first decimal point.

In addition, in the case of a conventional multi-measurement sensor including a single sensor, since measurement is performed by action of one sensor, there is a problem that biological information may not be measured for various parts of an object, and there is a limit that information measured by one sensor is unreliable.

Korean Patent Application Publication No. 10-2014-0119795 relates to a large-area temperature sensor including a plurality of temperature-related resistors connected in series and in parallel to form a network topologically equivalent to a square resistor network, and terminals capable of measuring the average resistance value thereof, wherein the resistors are supported on a substrate having a reduced size relative to an initial size thereof without substantially changing the average resistance value.

Korean Patent No. 10-1133082 relates to a temperature sensor capable of multi-point temperature measurement including a thermocouple part having a plurality of thermocouples in a bundle shape, a connector positioned at the rear thereof, a fixture positioned at the tip thereof, and sensing points for sensing temperature in a plurality of regions set along the longitudinal direction; a plurality of metal sleeves disposed on one side of the area where the sensing points are formed and arranged to surround a part of the thermocouple; a plurality of metal bellows disposed to surround each of the sleeves; and a plurality of metal pipes surrounding the sensing points and connecting adjacent bellows to each other, wherein the sensing points are disposed in the inner region of the pipe, and the pipe is provided with a plurality of through holes spaced apart from each other in the circumferential direction at positions corresponding to the sensing points.

SUMMARY OF THE DISCLOSURE

Therefore, the present invention has been made in view of the above problems, and it is one object of the present invention to provide a device for measuring biological information including a sensor array capable of real-time measurement of biological information including heart rate, oxygen saturation, and temperature of the skin tissues in a non-invasive manner in a short time by sensing the reflectance or transmittance of light reflected from the skin tissues, and a method of measuring biological information using the device.

It is another object of the present invention to provide a device for measuring biological information including a sensor array and a method of measuring biological information using the device, wherein the sensor array includes sensors each including a light amplification phototransistor including a channel region, a local gate electrode, non-overlapping regions, and a phototransistor, wherein the channel region is formed of a transition metal chalcogen compound, and non-overlapping regions do not overlap the local gate electrode and serve as photoconductors of the channel region for amplifying photoconductivity.

It is another object of the present invention to provide a device for measuring biological information including a sensor array and a method of measuring biological information using the device. When the device or the method is used, an average value for biological tissues is measured based on resistance values of a plurality of island networks. Thus, an error for different resistance values measured by a plurality of sensors may be reduced.

It is another object of the present invention to provide a device for measuring biological information including a sensor array and a method of measuring biological information using the device, wherein the device is manufactured in a patch type that is flexible and has good biocompatibility and does not slip on the skin, and the device is capable of accurately measuring absorption information or resistance values of the skin tissues corresponding to a site to be measured and transmitting an average value of the biological information measured based on the absorption information or resistance value to the outside. Therefore, the biological information transmitted in real time may help in treatment and prevention.

It is yet another object of the present invention to provide a device for measuring biological information including a sensor array and a method of measuring biological information using the device, wherein the device is capable of measuring an average value of at least one of oxygen saturation, heart rate, and temperature for a wide contact area and various parts of the skin tissues to be measured based on a plurality of sensors, and thus an error for different absorption information or resistance values measured by sensors may be reduced.

In accordance with one aspect of the present invention, provided is a device for measuring biological information including a sensor array, wherein the device includes a light source for generating light; a sensor array formed on a substrate and including a plurality of sensors, wherein each of the sensors is connected to a switching thin film transistor, and the sensors are responsible for amplifying photoreactivity of light reflected from the skin tissues or transmitted through the skin tissues after being emitted from the light source and responsible for outputting absorption information from the light having amplified photoreactivity to map biological information associated with tissue activities and functions of the skin tissues; and an average value measurement part for measuring an average value of the biological information detected by the sensor array based on the absorption information output from the sensors.

The sensor may include one or more light amplification phototransistors arranged in an active matrix form.

The light amplification phototransistor may include a local gate electrode, a source electrode, a drain electrode, and a channel region formed between the source electrode and the drain electrode and including non-overlapping regions not overlapping the gate electrode, wherein the non-overlapping regions serve as photoconductors for amplifying photoconductivity.

In addition, the non-overlapping region may be formed both in the lateral direction of the source electrode and in the lateral direction of the drain electrode, or in the lateral direction of any one of the source electrode and the drain electrode, and the channel region may be formed of a transition metal chalcogen compound (transition metal dichalcogenide).

The biological information may be associated with tissue activities and functions associated with at least one of heart rate and oxygen saturation, the sensor array may be connected to an IC circuit formed on the substrate to form a patch-like structure, and the substrate may be formed of at least one of paper, a polymer, woven fabric, and metal foil.

In addition, a device for measuring biological information including a sensor array according to an embodiment of the present invention may further include a communication module for transmitting an average value of the measured biological information to the outside and a controller for controlling the average value measurement part to measure an average value of the biological information based on absorption information measured by at least one of the sensors in response to a control command received from the communication module.

In accordance with another aspect of the present invention, provided is a device for measuring biological information including a sensor array, wherein the device includes a sensor array formed on a substrate and including a plurality of sensors forming an island network in which nodes and a plurality of multi-channels are connected, wherein the sensor includes terminals for measuring resistance values with respect to tissue activities and functions of the skin tissues; and an average value measurement part for measuring an average value of biological information detected by the sensor arrays based on the resistance values measured by the terminals.

In the sensor array, each of the sensors may perform calibration to minimize offset voltage generated according to changes in the resistance values of a temperature sensing element, and measure resistance values for mapping the biological information.

In the sensor, a plurality of multi-channels formed in a meander pattern may be connected to the nodes and arranged in a matrix form on the substrate.

In addition, the multi-channels may be thermistors. Each multi-channel may have a length-to-width ratio of less than 100. Each multi-channel may be formed at an angle of at least one of 0°, 90°, 45°, −45°, and −90° with respect to a horizontal direction to the substrate, so that change in the resistance values to the skin tissues may be minimized.

The sensor array may determine the presence or absence of offset voltage according to changes in the resistance values of the temperature sensing element at every predetermined period, and repeat the calibration process stepwise until the offset voltage is removed.

The average value measurement part may measure an average value of the remaining sensors except specific ones among the sensors based on the measured resistance values. When the average value is measured by the average value measurement part, a sensor having the highest or lowest temperature among the resistance values measured by the sensors may be excluded, and a sensor for detecting a sudden temperature change exceeding a predetermined reference among the sensors may be excluded.

In addition, a device for measuring biological information including a sensor array according to another embodiment of the present invention may further include a communication module for transmitting the measured average value to the outside; a controller for controlling the average value measurement part to measure an average value of the biological information based on resistance values measured by at least one of the sensors in response to a control command received from the communication module; and a power supply for supplying driving power.

When a resistance value measured by the sensor array changes to a predetermined value or more, the controller may apply additional current to the sensors, so that the sensors perform calibration for minimizing offset voltage.

In addition, a device for measuring biological information including a sensor array according to another embodiment of the present invention may further include a selection switch for selectively measuring resistance values of the sensors.

In accordance with yet another aspect of the present invention, provided is a method of measuring biological information using a sensor array, the method including a step of detecting the presence or absence of changes in the resistance values of a temperature sensing element by each of the sensors; a step of detecting temperature by performing calibration to minimize offset voltage generated according to change in the resistance values when change in the resistance values is detected; and a step of measuring an average value of the remaining sensors except specific ones among the sensors based on the detected temperature.

As apparent from the foregoing, the present invention advantageously provides a device for measuring biological information including a sensor array capable of real-time measurement of biological information including heart rate, oxygen saturation, and temperature of the skin tissues in a non-invasive manner in a short time by detecting the reflectance or transmittance of light reflected from the skin tissues.

In addition, according to an embodiment of the present invention, the sensor array included in the device of the present invention can be equipped with sensors each including a light amplification phototransistor including a channel region, a local gate electrode, non-overlapping regions, and a phototransistor, wherein the channel region is formed of a transition metal chalcogen compound, and non-overlapping regions do not overlap the local gate electrode and serve as photoconductors of the channel region for amplifying photoconductivity.

In addition, according to an embodiment of the present invention, when the device of the present invention is used, an average value for biological tissues is measured based on resistance values of a plurality of island networks. Thus, an error for different resistance values measured by a plurality of sensors can be reduced.

In addition, according to an embodiment of the present invention, the device of the present invention is manufactured in a patch type that is flexible and has good biocompatibility and does not slip on the skin, and the device is capable of accurately measuring absorption information or resistance values of the skin tissues corresponding to a site to be measured and transmitting an average value of the biological information measured based on the absorption information or resistance value to the outside. Therefore, the biological information transmitted in real time can help in treatment and prevention.

In addition, according to an embodiment of the present invention, the device is capable of measuring an average value of at least one of oxygen saturation, heart rate, and temperature for a wide contact area and various parts of the skin tissues to be measured based on a plurality of sensors, and thus an error for different absorption information or resistance values measured by sensors can be reduced.

DETAILED DESCRIPTION OF THE DISCLOSURE

Figure 1:
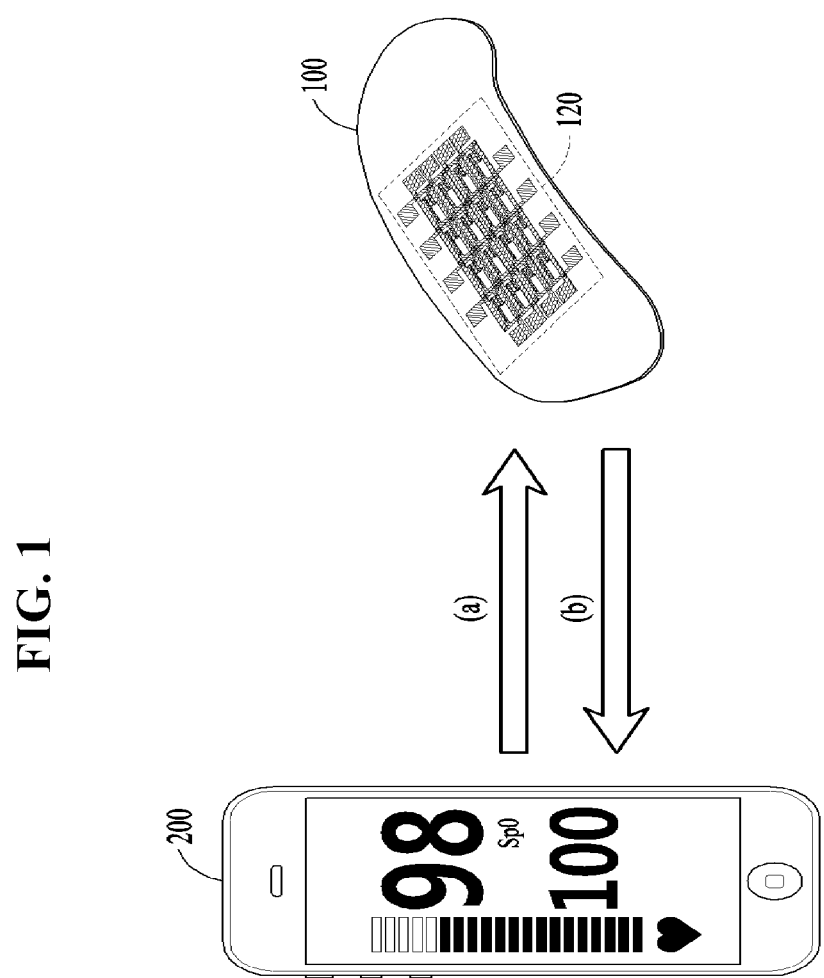
FIG. 1 illustrates a device for measuring biological information including a sensor array according to an embodiment of the present invention.

The present invention will now be described more fully with reference to the accompanying drawings and contents disclosed in the drawings. However, the present invention should not be construed as limited to the exemplary embodiments described herein.

The terms used in the present specification are used to explain a specific exemplary embodiment and not to limit the present inventive concept. Thus, the expression of singularity in the present specification includes the expression of plurality unless clearly specified otherwise in context. It will be further understood that the terms "comprise" and/or "comprising", when used in this specification, specify the presence of stated components, steps, operations, and/or elements, but do not preclude the presence or addition of one or more other components, steps, operations, and/or elements thereof.

It should not be understood that arbitrary aspects or designs disclosed in "embodiments", "examples", "aspects", etc. used in the specification are more satisfactory or advantageous than other aspects or designs.

In addition, the expression "or" means "inclusive or" rather than "exclusive or". That is, unless otherwise mentioned or clearly inferred from context, the expression "x uses a or b" means any one of natural inclusive permutations.

In addition, as used in the description of the invention and the appended claims, the singular forms "a", "an" and "the" are intended to include the plural forms as well, unless context clearly indicates otherwise.

In addition, terms such as "first" and "second" are used herein merely to describe a variety of constituent elements, but the constituent elements are not limited by the terms. The terms are used only for the purpose of distinguishing one constituent element from another constituent element.

Unless otherwise defined, all terms (including technical and scientific terms) used herein have the same meaning as commonly understood by one of ordinary skill in the art. It will be further understood that terms, such as those defined in commonly used dictionaries, should be interpreted as having a meaning that is consistent with their meaning in the context of the relevant art and the present invention, and will not be interpreted in an idealized or overly formal sense unless expressly so defined herein.

Meanwhile, in the following description of the present invention, a detailed description of known functions and configurations incorporated herein will be omitted when it may make the subject matter of the present invention unclear. The terms used in the specification are defined in consideration of functions used in the present invention, and can be changed according to the intent or conventionally used methods of clients, operators, and users. Accordingly, definitions of the terms should be understood on the basis of the entire description of the present specification.

FIG. 1 illustrates a device for measuring biological information including a sensor array according to an embodiment of the present invention.

Referring to FIG. 1, a device for measuring biological information including a sensor array 100 according to an embodiment of the present invention includes a sensor array 120.

The sensor array 120 includes a plurality of sensors and is formed on a substrate. The sensors are connected to a switching thin film transistor, amplify photoreactivity of light reflected from the skin tissues or transmitted through the skin tissues after being emitted from a light source, and output absorption information from the light having amplified photoreactivity to map biological information associated with tissue activities and functions of the skin tissues.

According to one embodiment, the device for measuring biological information including a sensor array 100 according to an embodiment of the present invention may further include one or more of a light source (not shown), an average value measurement part (not shown), a communication module (not shown), a controller (not shown), and a power supply (not shown) in addition to the sensor array 120.

The light source may generate light, and the average value measurement part may measure an average value of biological information detected by the sensor array 120 based on absorption information output from sensors.

In addition, the communication module may transmit the measured average value of biological information to the outside, the controller may perform control to measure an average value of biological information, and the power supply may supply driving power to at least one of the light source, the average value measurement part, the communication module, and the controller.

Referring again to FIG. 1, the device for measuring biological information including a sensor array 100 according to an embodiment of the present invention may transmit at least one (b) of absorption information output from sensors and an average value of biological information measured in an average value measurement part to a terminal.

Herein, the biological information may refer to at least one of heart rate (pulse), oxygen saturation, and temperature measured based on absorption information obtained from the skin tissues of a user (patient).

In addition, a terminal 200 may provide a user with at least one of heart rate, oxygen saturation, and temperature in real time based on at least one of absorption information and an average value of biological information received from the device for measuring biological information including a sensor array 100.

For example, based on a predetermined reference value for at least one of heart rate, oxygen saturation, and temperature, the terminal 200 may provide at least one of absorption information and an average value of biological information received from the device for measuring biological information including a sensor array 100 to a user as at least one of a value, a percentage, an image, a picture, a graph, and a message. According to one embodiment, notification information including at least one of a warning message, alarm, voice, light, and vibration may be provided.

In addition, the terminal 200 may control the device for measuring biological information including a sensor array 100 according to a control command input by a user.

For example, the terminal 200 may transmit a control command (a) to the device for measuring biological information including a sensor array 100 based on a control command input by a user, so that the device measures at least one of the heart rate, oxygen saturation, and temperature of the user, or may transmit the control command (a), so that a light source for generating light is controlled to measure an average value.

In addition, the terminal 200 may perform control so that arbitrary sensors among a plurality of sensors are selected according to a measurement target part of the body to be measured, and may transmit the control command (a) to control a sensor array including the sensors.

According to one embodiment, the terminal 200 may be at least one of a terminal, a smart phone, a table PC, and a PC carried by a user, without being limited thereto.

In addition, the terminal 200 may transmit at least one of absorption information and an average value of biological information received from the device for measuring biological information including a sensor array 100 to an integrated server (not shown).

The integrated server may comprehensively manage at least one of absorption information and an average value of biological information received from the terminal 200, and may analyze change trend of data related to a user and health state of the user and transmit the analyzed data to the terminal 200.

In addition, the integration server may provide user's data to healthcare professionals, hospitals, health centers, and professionals for healthcare guidance. Based on the analyzed data, at least one of exercise, food, lifestyle, and prescription may be provided for the user.

In addition, according to one embodiment, a configuration of the integrated server may be controlled through the terminal 200.

Figure 2:
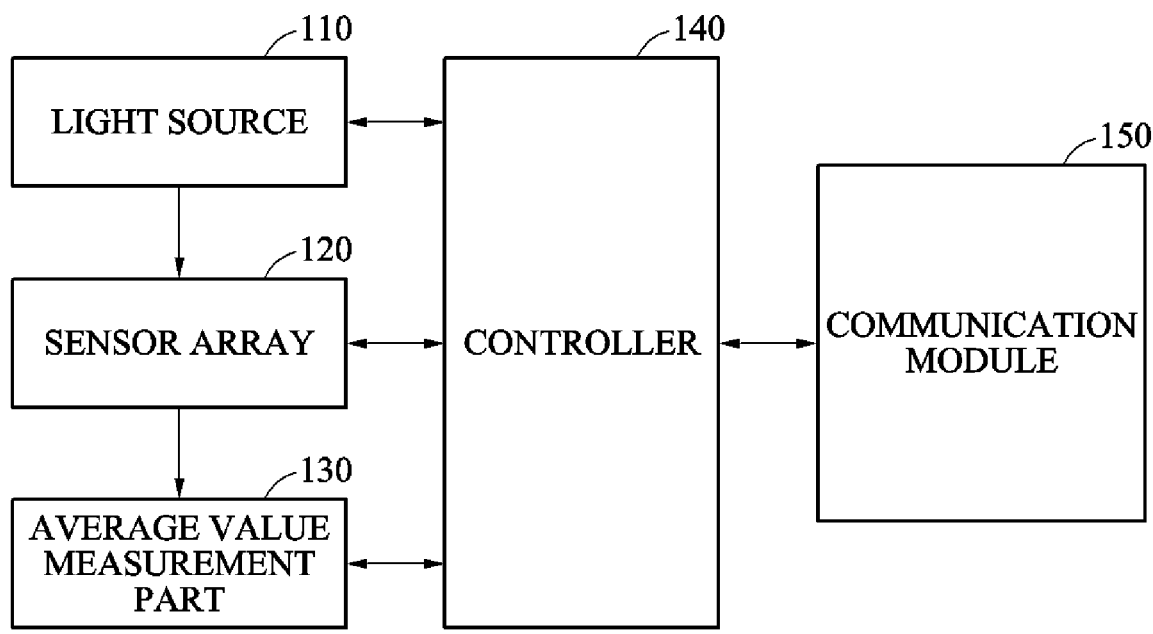
FIG. 2 is a block diagram for explaining a configuration of a device for measuring biological information including a sensor array according to an embodiment of the present invention.

FIG. 2 is a block diagram for explaining a configuration of a device for measuring biological information including a sensor array according to an embodiment of the present invention.

Referring to FIG. 2, the device for measuring biological information including a sensor array 100 according to an embodiment of the present invention outputs absorption information for matching biological information associated with tissue activities and functions of the skin tissues, and measures an average value of the biological information based on the output absorption information.

The device for measuring biological information including a sensor array 100 according to an embodiment of the present invention includes a light source 110, the sensor array 120, and an average value measurement part 130.

The light source 110 generates light. Herein, the light may be reflected from the skin tissues or transmitted through the skin tissues and sensed by sensors, and may have a wavelength in the infrared range to the ultraviolet range.

The sensor array 120 is formed on a substrate and includes a plurality of sensors, wherein the sensors are connected to switching thin film transistors, and serve to amplify photoreactivity of light, which is generated by the light source 110 and reflected from the skin tissues or transmitted through the skin tissues, and output absorption information from the light having amplified photoreactivity to map biological information associated with tissue activities and functions of the skin tissues.

For example, light generated by the light source 110 is reflected from the skin tissues or transmitted through the skin tissues and is incident on sensors attached to the skin tissues. Then, the sensors may amplify photoreactivity of the incident light, and then detect the light and output absorption information of the skin tissues.

The sensor array 120 may be connected to an IC circuit formed on a substrate and formed in a patch-like structure.

IC circuits may perform signal filtering, amplification, digitization, and processing functions by using integration techniques. According to one embodiment, the IC circuit may be an integrated and multi-functional IC sensor that processes signals in a substrate.

In addition, the patch-like structure may have various sizes and shapes according to the area and characteristics of the adhesive portion of a body surface, and may include a medical grade skin contact adhesive suitable for application to the skin. Also, the patch-like structure may have at least one of circular, square, rectangular, rhombic, cruciform, curved, and X-shaped shapes having various sizes.

The substrate included in the device for measuring biological information including a sensor array 100 according to an embodiment of the present invention may include the sensor array 120, and may be formed of at least one of paper, a polymer, woven fabric, and metal foil.

According to one embodiment, the substrate may be a flexible substrate that can be attached to the skin, and may be formed of at least one of polyimide, polycarbonate, polyacrylate, polyetherimide, polyethersulfone, polyethylene terephthalate, and polyethylene naphthalate.

Since the above-described materials may be used at a high process temperature of 450° C. or more, deterioration of the characteristics of the light amplification phototransistor may be minimized in manufacturing the light amplification phototransistor.

In addition, since a flexible substrate has a property of being bent or stretched by heat, it is difficult to precisely form a pattern of a light amplification phototransistor thereon.

Thus, in the case of a device for measuring biological information including a sensor array according to an embodiment of the present invention, when a flexible substrate is manufactured, a sacrificial layer is spin-coated with a liquid polymer material, so that heat or mechanical shock may be mitigated.

Hereinafter, the sensor array 120 will be described in detail with reference to FIG. 3.

Figure 3:
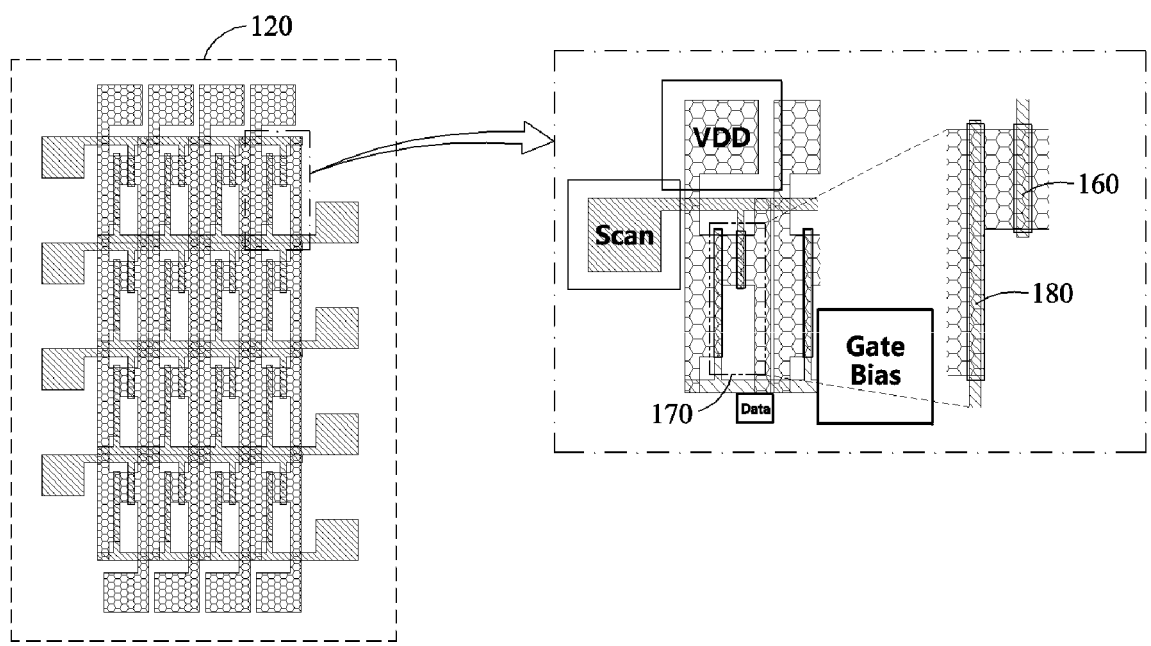
FIG. 3 illustrates a detailed configuration of a sensor array according to an embodiment of the present invention.

FIG. 3 illustrates a detailed configuration of a sensor array according to an embodiment of the present invention.

Referring to FIG. 3, the sensor array 120 may include a plurality of sensors 170, and each of the sensors 170 may include a light amplification phototransistor 180 and may be connected to a switching thin film transistor 160.

In addition, the sensors 170 may be connected to driving voltage (Vdd), scan signal (Scan), and gate bias.

According to one embodiment, the sensors 170 included in the sensor array 120 may be provided in plural, but the number, area, size, and shape of the sensors 170 may vary depending on embodiments, and thus the present invention is not limited thereto. Hereinafter, the sensors 170 and the switching thin film transistor 160 will be described in detail with reference to FIG. 4.

FIG. 4 illustrates a structure and a circuit diagram of a sensor-based sensor array according to an embodiment of the present invention.

Figure 4A:
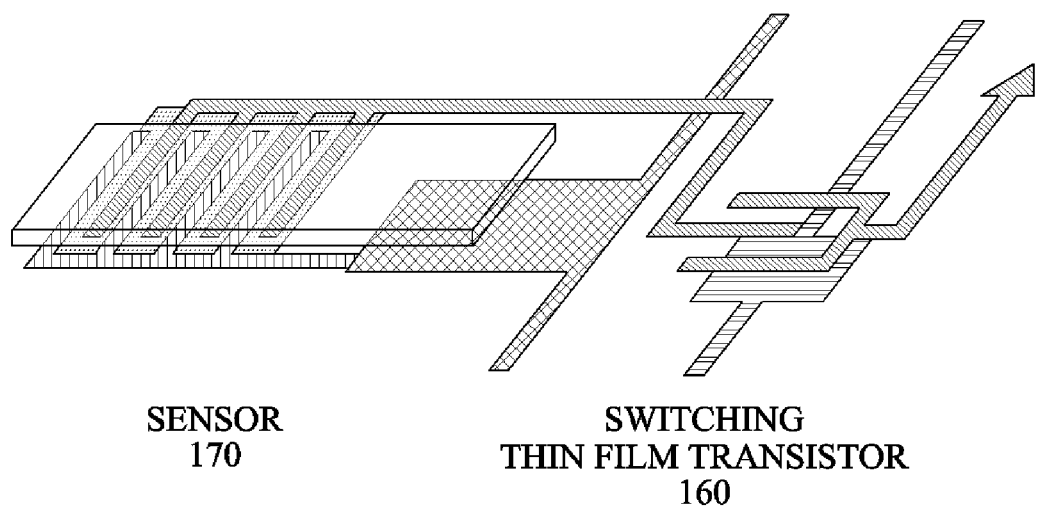
FIGS. 4A and 4B illustrate a structure and a circuit diagram of a sensor-based sensor array according to an embodiment of the present invention.
Figure 4B:
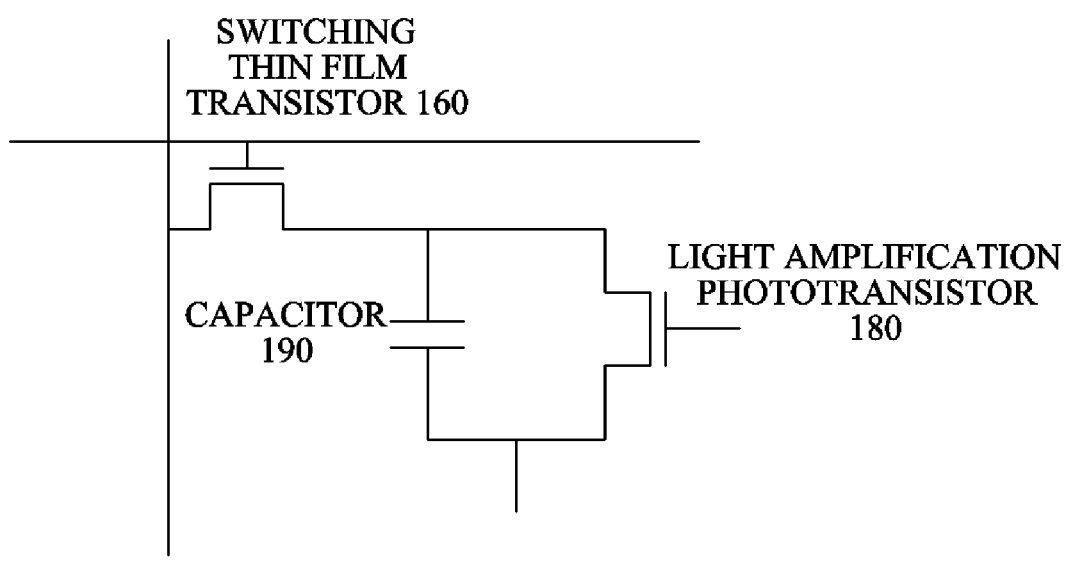

More specifically, FIG. 4A illustrates a local structure of a sensor-based sensor array according to an embodiment of the present invention, and FIG. 4B illustrates a circuit diagram of a sensor-based sensor array according to an embodiment of the present invention.

Referring to FIG. 4A, a device for measuring biological information including a sensor array according to an embodiment of the present invention includes the sensors 170 each including one or more light amplification phototransistors arranged in an active matrix form and includes the switching thin film transistor 160.

The sensor array 120 may include the sensors 170 to which DC biases are applied, wherein the DC biases are arranged in a matrix form to maximize photoreactivity of a circuit that outputs absorption information.

In addition, when the gate pulse signal of light scattered by the skin tissues is transmitted to the switching thin film transistor 160, the switching thin film transistor 160 may be turned on, the sensors 170 connected to the drain of the switching thin film transistor 160 may be turned on in response to light absorption, and a capacitor 190 may be reset by a reference voltage.

In addition, the sensors 170 may sense light reflected from the skin tissues and amplify photoreactivity. The sensors 170 may output on/off state according to absorption state of the sensed light and output absorption information accordingly.

Referring to FIG. 4B, the gate of the switching thin film transistor 160 arranged in a matrix form is connected to a gate line, the source of the switching thin film transistor 160 is connected to a data line, and the drain of the switching thin film transistor 160 is connected to the source of the light amplification phototransistor 180.

In the sensor-based sensor array, each gate may operate as a shift resistor while each bus line is connected to an external touch read-out IC (R/O IC).

In addition, the gate line and the data line of the sensor-based sensor array may be respectively connected to a gate driving circuit and a data driving circuit, and each connected line and circuit may be supplied with driving signal voltage and input data signal voltage.

Referring again to FIG. 2, the average value measurement part 130 included in the device for measuring biological information including a sensor array 100 according to an embodiment of the present invention measures an average value of biological information detected by the sensor array 120 based on absorption information output from sensors.

The average value measurement part 130 may measure an average value of biological information based on absorption information of the skin tissues measured by the sensors.

According to one embodiment, the average value measurement part 130 may measure an average value of integrated biological information for different regions based on absorption information received from the sensor array 120 attached to different regions of the skin.

The biological information may be associated with tissue activities and functions associated with at least one of heart rate, oxygen saturation, and temperature, and the biological information may refer to information obtained using a pulse oximeter.

The device for measuring biological information including a sensor array 100 according to an embodiment of the present invention may further include a controller 140 and a communication module 150.

The controller 140 may control the average value measurement part 130 to measure an average value of biological information based on absorption information measured by at least one of a plurality of sensors in response to a control command received from the communication module 150.

For example, the controller 140 may control the average value measurement part 130 to measure an average value of biological information using only absorption information measured by sensors located at specific locations on the sensor array 120 in response to a control command received form an external terminal.

According to one embodiment, the controller 140 may be disposed on a substrate, but may be located outside the substrate to control at least one of the light source 110, the sensor array 120, the average value measurement part 130, and the communication module 150.

The communication module 150 may transmit the measured average value of biological information to the outside.

The communication module 150 may transmit and receive at least one of an average value of biological information and absorption information with different transmission bandwidths. According to coverage, at least one of ZigBee, Bluetooth, GeoWave, and Wi-Fi may be applied to the communication module 150.

In addition, an average value of biological information measured using the device for measuring biological information including a sensor array 100 according to an embodiment of the present invention may be transmitted from the communication module 150 to at least one of a user terminal, an integrated server, a healthcare institution, and a device for measuring biological information including different sensor arrays.

In addition, the device for measuring biological information including a sensor array 100 according to an embodiment of the present invention may further include a power supply (not shown) and a selection switch (not shown).

The power supply may supply driving power to at least one of the light source 110, the sensor array 120, the average value measurement part 130, the controller 140, and the communication module 150.

For example, the power supply may be composed of an active element using an ultra-small rechargeable battery or an ultra-small super-capacitor.

According to one embodiment, the power supply may be a primary cell such as a coin cell or a secondary cell such as a lithium polymer battery. When the power supply is a secondary cell, the power supply may be charged by an external power source (e.g., a terminal). When the power supply is a primary cell such as a coin cell, the power supply may be replaced with a new one.

The selection switch may selectively measure resistance values of the sensors.

In the device for measuring biological information including a sensor array 100 according to an embodiment of the present invention, at least one of the average value measurement part 130, the controller 140, the power supply, and the selection switch may be located outside a patch-type substrate in accordance with embodiments of the present invention.

Figure 5:
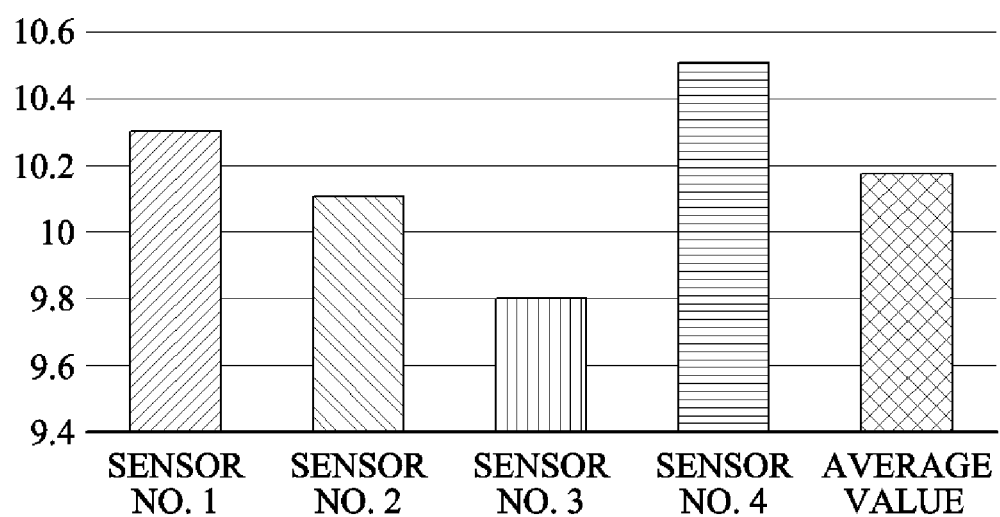
FIG. 5 is a graph showing an average value measured by a sensor array including sensors according to an embodiment of the present invention.

FIG. 5 is a graph showing an average value measured by a sensor array including sensors according to an embodiment of the present invention.

More specifically, FIG. 5 is a graph showing an average value of biological information (pulse oximeter) measured by a device for measuring biological information including a single sensor.

Referring to FIG. 5, a pulse oximeter value measured by a device for measuring biological information including sensor No. 1 is about 10.3, and a pulse oximeter value measured by a device for measuring biological information including sensor No. 2 is about 10.1.

In addition, a pulse oximeter value measured by a device for measuring biological information including sensor No. 3 is about 9.8, and a pulse oximeter value measured by a device for measuring biological information including sensor No. 4 is about 10.5 (although five sensors are illustrated in FIG. 5 as an example, the present invention is not limited to the above-described number of sensors, and the number of sensors may be determined without limitation).

That is, as shown in FIG. 5, in the case of a device for measuring biological information including a single sensor, pulse oximeter values change depending on the position or area of the sensor attached to a measurement site. Therefore, there is a limit to accurately measure pulse oximeter values of biological tissues to be measured.

Therefore, it can be seen that the device for measuring biological information including a sensor array including a plurality of sensors according to an embodiment of the present invention has higher accuracy and reliability for an average value of pulse oximeters calculated than a device for measuring biological information including a single sensor. In addition, when the device of the present invention is used, error caused by external factors is small. Thus, pulse oximeters with high accuracy for the skin tissues may be measured constantly within a small error range.

Figure 6:
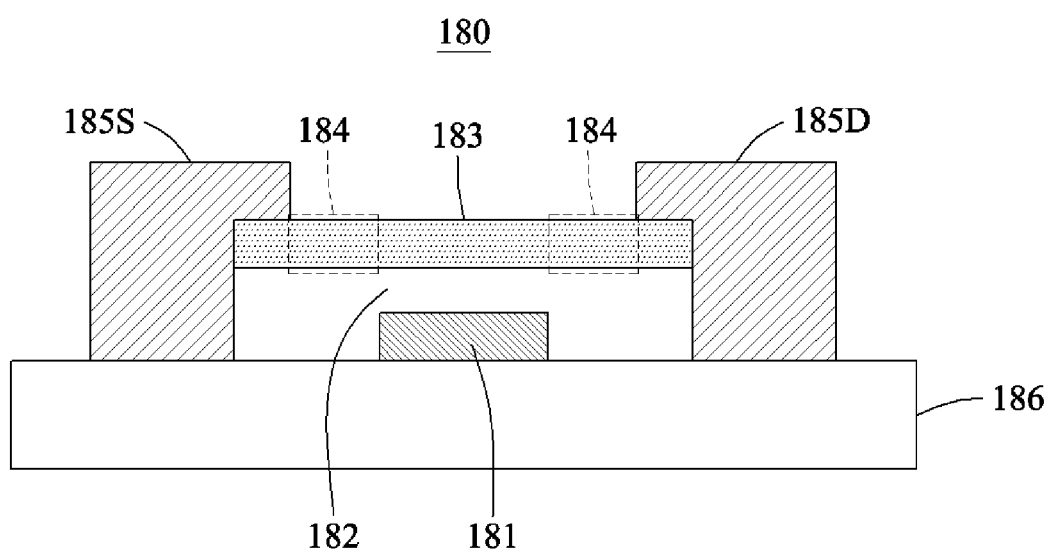
FIG. 6 illustrates a light amplification phototransistor included in a sensor according to an embodiment of the present invention.
Figure 7:
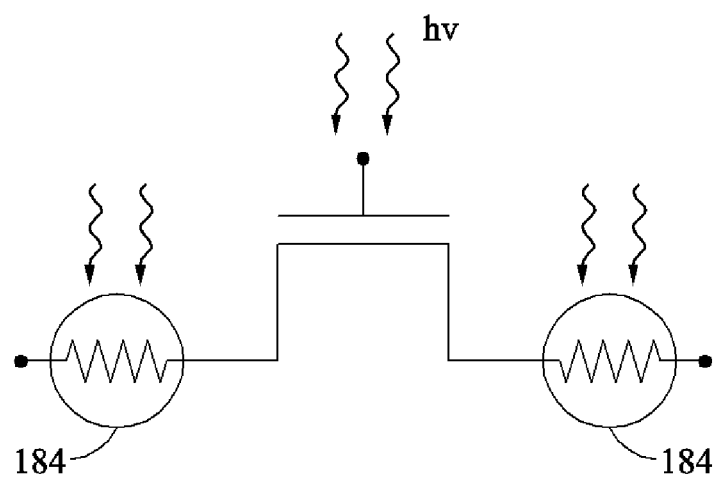
FIG. 7 is a circuit diagram of a light amplification phototransistor included in a sensor according to an embodiment of the present invention.

FIG. 6 illustrates a light amplification phototransistor included in a sensor according to an embodiment of the present invention, and FIG. 7 is a circuit diagram of a light amplification phototransistor included in a sensor according to an embodiment of the present invention.

The light amplification phototransistor of the present invention includes a gate electrode, a source electrode, a drain electrode, and a channel region formed between the source electrode and the drain electrode and including non-overlapping regions not overlapping the gate electrode, wherein the non-overlapping regions serve as photoconductors for amplifying photoconductivity.

According to an embodiment, the gate electrode may have a local top gate structure or a local bottom gate structure.

Referring to FIG. 6, a light amplification phototransistor having a bottom gate structure is illustrated. The light amplification phototransistor 180 according to an embodiment of the present invention includes a local bottom gate electrode 181 formed on a substrate 186, a gate insulating layer 182 formed to cover the local bottom gate electrode 181, a source electrode 185S formed on one side of the gate insulating layer 182 and a drain electrode 185D formed on the other side of the gate insulating layer 182, and a channel region 183 formed on the gate insulating layer 182 and formed between the source electrode 185S and the drain electrode 185D.

The local bottom gate electrode 181 is formed on the substrate 186, and the gate insulating layer 182 is formed on the substrate 186 to cover the local bottom gate electrode 181.

The source electrode 185S is formed on one side of the gate insulating layer 182 and the drain electrode 185D is formed on the other side of the gate insulating layer 182.

The local bottom gate electrode 181, the source electrode 185S, and the drain electrode 185D may be made of at least one of metals and transparent conductive materials, and the metals are any one of gold (Au), titanium (Ti), aluminum (Al), and palladium (Pd), without being limited thereto. Any metals used in the technical field of the present invention may be used as the metals. In addition, the transparent conductive materials may be at least one of amorphous oxides, crystalline oxides, graphene, and polymer organic materials.

According to one embodiment, the local bottom gate electrode 181, the source electrode 185S, and the drain electrode 185D may be made of a transparent conductive material, and the transparent conductive material may be at least one of indium zinc oxide (IZO), indium thin oxide (ITO), and graphene.

The channel region 183 is formed on the gate insulating layer 182 and is formed between the source electrode 185S and the drain electrode 185D, and includes non-overlapping regions 184 not overlapping the local bottom gate electrode 181.

As shown in FIG. 7, when no light is applied, the non-overlapping regions 184 of the light amplification phototransistor 180 according to the present invention act as external series resistance even when bias is applied to the gate electrode. However, when light is applied, resistance is lowered and conductivity is increased in the non-overlapping regions 184, so that the non-overlapping regions 184 act as a photoconductor for amplifying photoconductivity.

The channel region 183 may be formed of at least one of transition metal chalcogen compounds (transition metal dichalcogenide), silicon (Si) materials, and silicon oxide, and the transition metal chalcogen compound may be formed as a single layer or multiple layers.

Compared to one-dimensional materials, it is easier to manufacture complex structures using two-dimensional materials. Therefore, two-dimensional materials are suitable for use in manufacturing next-generation nanoelectronic devices. Among these two-dimensional materials, a two-dimensional transition metal chalcogen compound (2D transition metal dichalcogenide) may be at least one of molybdenum disulfide ($MoS_2$), molybdenum diselenide ($MoSe_2$), tungsten diselenide ($WSe_2$), molybdenum ditelluride ($MoTe_2$), and tin diselenide ($SnSe_2$).

In addition, the two-dimensional transition metal chalcogen compounds generally have a band-gap of 2 eV or less, and thus may absorb light having a wavelength of 1,500 nm or less.

As shown in FIG. 6, in the light amplification phototransistor according to an embodiment of the present invention 180, the non-overlapping regions 184 are formed both in the lateral direction of the source electrode 185S and in the lateral direction of the drain electrode 185D. However, the present invention is not limited thereto, and the non-overlapping region of the light amplification phototransistor may be formed in the lateral direction of any one of the source electrode 185S and the drain electrode 185D.

In addition, in the light amplification phototransistor 180 of the present invention, the multiplelayer transition metal chalcogen compound is preferably formed in three or more layers.

Figure 8A:
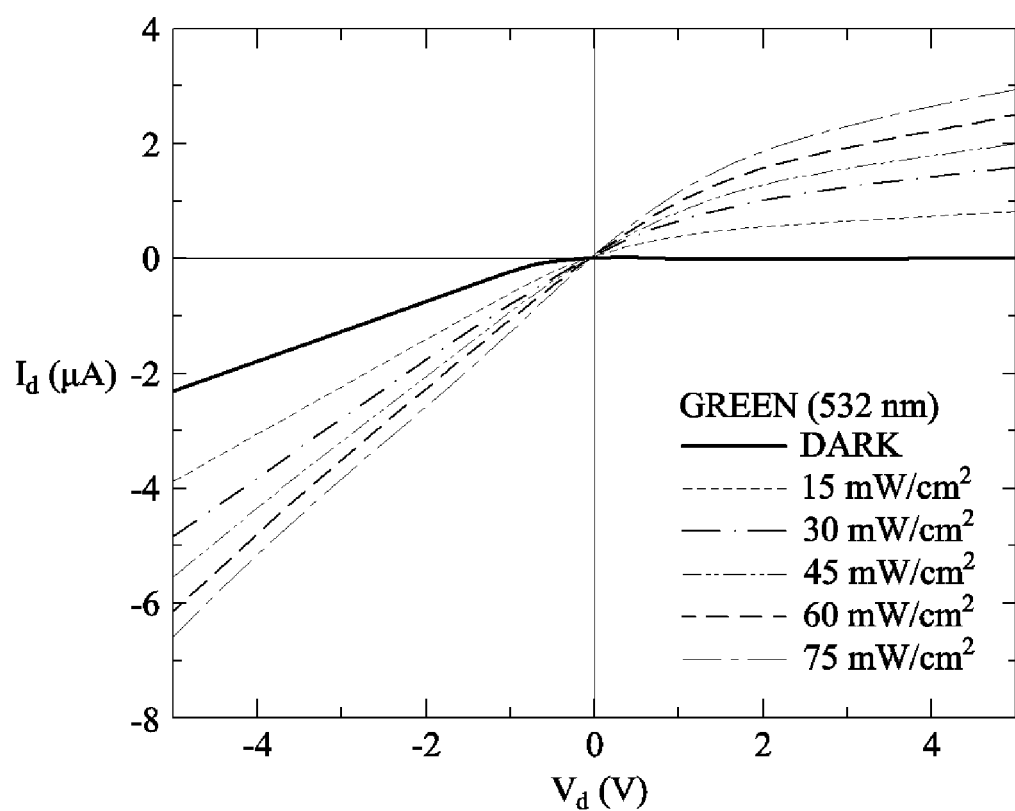
FIGS. 8A and 8B are graphs showing the characteristics of a light amplification phototransistor according to an embodiment of the present invention as a photoconductor.
Figure 8B:
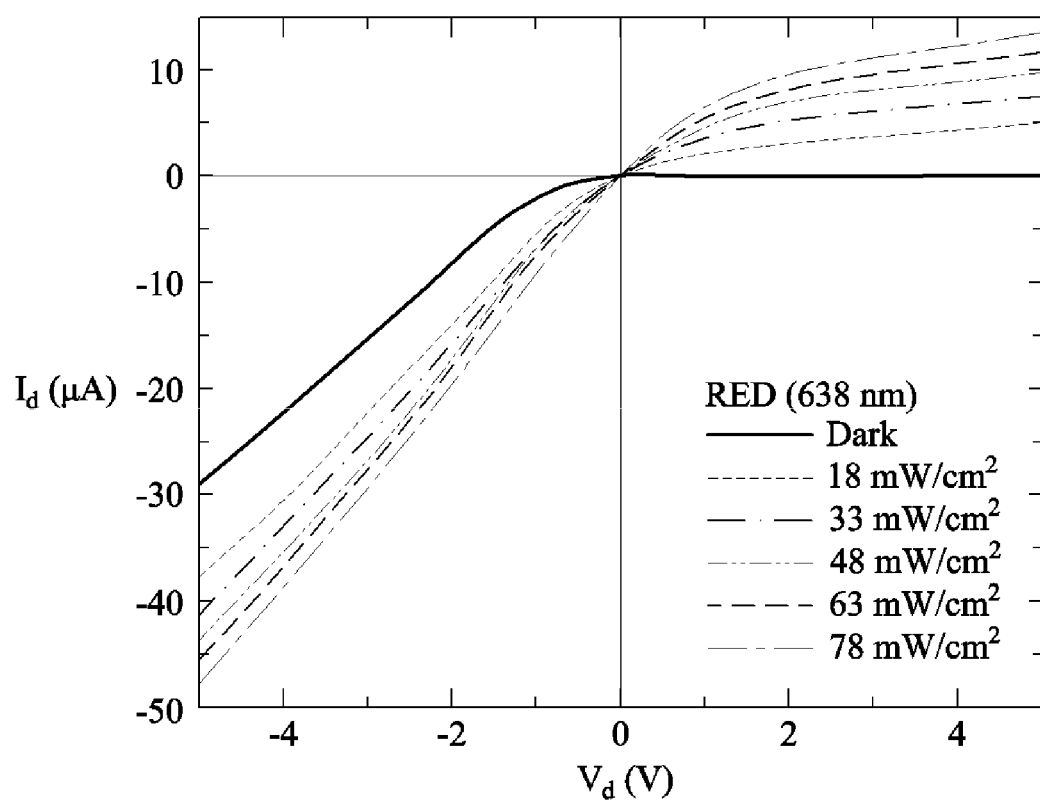

FIGS. 8A and 8B are graphs showing the characteristics of a light amplification phototransistor according to an embodiment of the present invention as a photoconductor. FIG. 8A is a characteristic graph in the case of irradiating green light (532 nm), and FIG. 8B is a characteristic graph in the case of irradiating red light (638 nm).

Referring to FIG. 8, compared with the case where there is no light irradiation, when a light amplification phototransistor according to an embodiment of the present invention is irradiated with light, resistance is lowered and conductivity is increased. In addition, as the wavelength of irradiation light becomes longer, the amount of drain current is increased.

Figure 9:
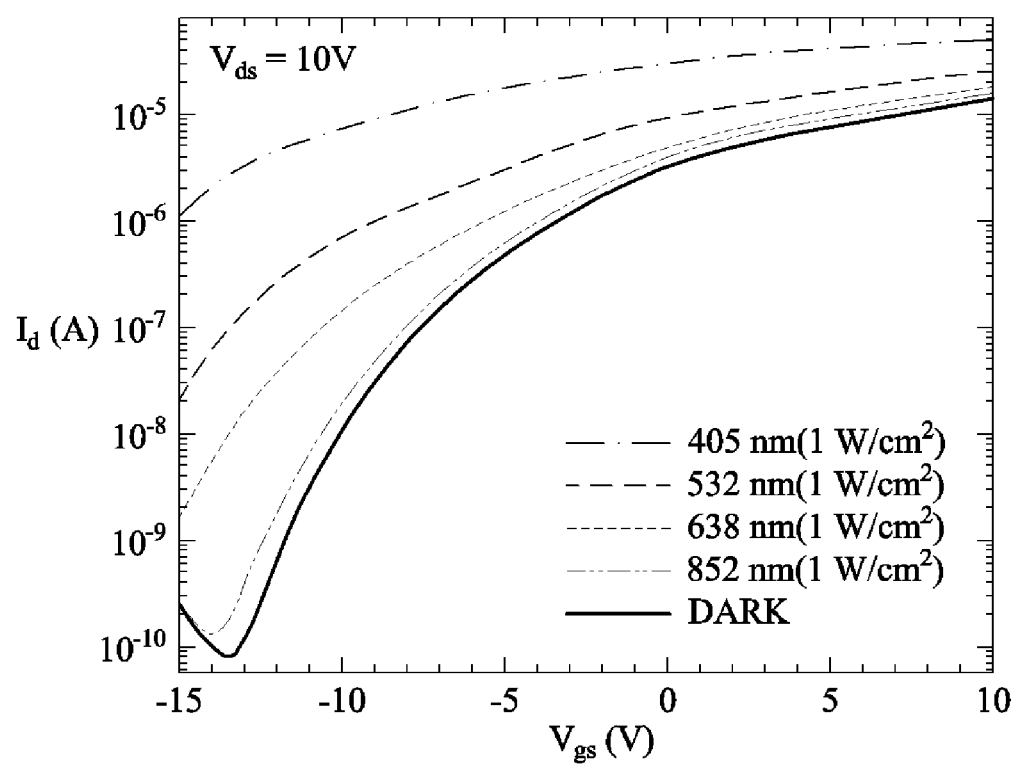
FIG. 9 is a graph showing transfer curves for a light amplification phototransistor according to an embodiment of the present invention.
Figure 10:
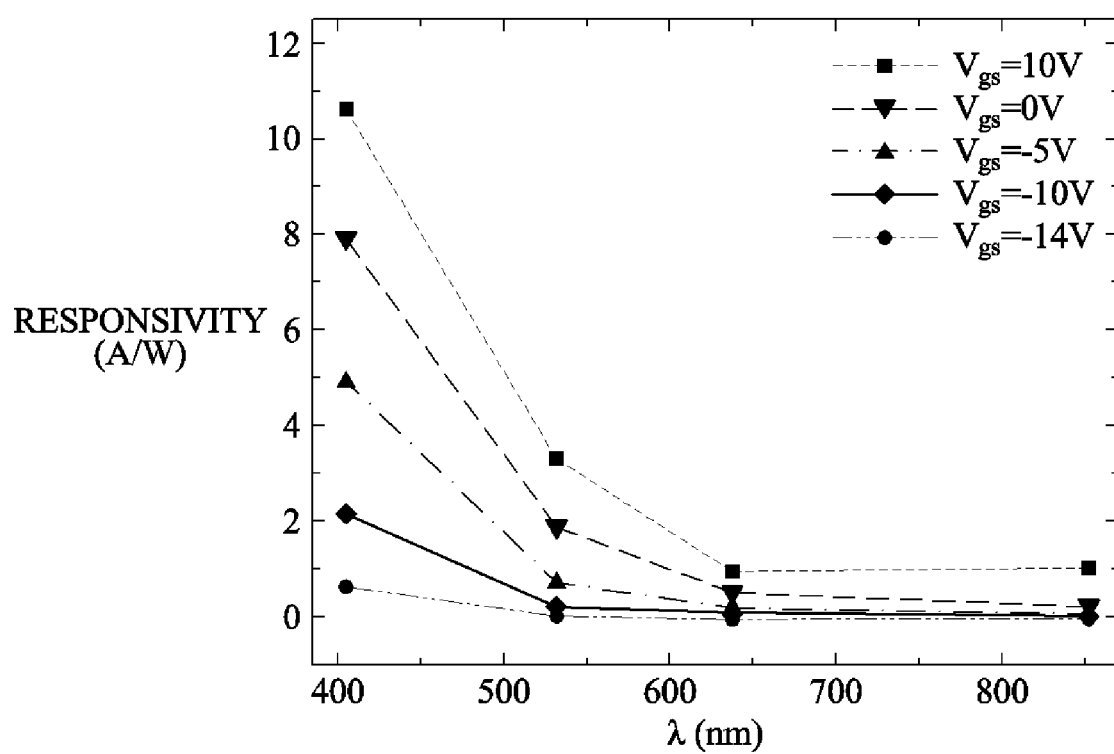
FIG. 10 is a graph showing photoreactivity of a light amplification phototransistor according to an embodiment of the present invention.

FIG. 9 is a graph showing transfer curves for a light amplification phototransistor according to an embodiment of the present invention, and FIG. 10 is a graph showing photoreactivity of a light amplification phototransistor according to an embodiment of the present invention.

Referring to FIGS. 9 and 10, when light is applied, in addition to a channel region overlapping a local gate electrode, electron-hole pairs are generated in the non-overlapping regions of a channel region serving as a photoconductor. As a result, the conductivity of the entire channel is amplified, and on-current in addition to off-current of the phototransistor is greatly increased.

As shown in FIGS. 9 and 10, photoreactivity of the light amplification phototransistor including a local gate electrode structure according to the present invention is increased about 100 to 1,000 times that of a conventional device (Woong Choi, et. al, Advanced Materials 24, 5382-5836 (2012)) including a common gate electrode structure and having a photoreactivity of 100 $mAW^{-1}$.

As shown in FIGS. 8 to 10, the light amplification phototransistor of the present invention may amplify optical gain and photoreactivity through a structure in which a photoconductor and a phototransistor are combined by forming a local gate electrode.

Figure 11:
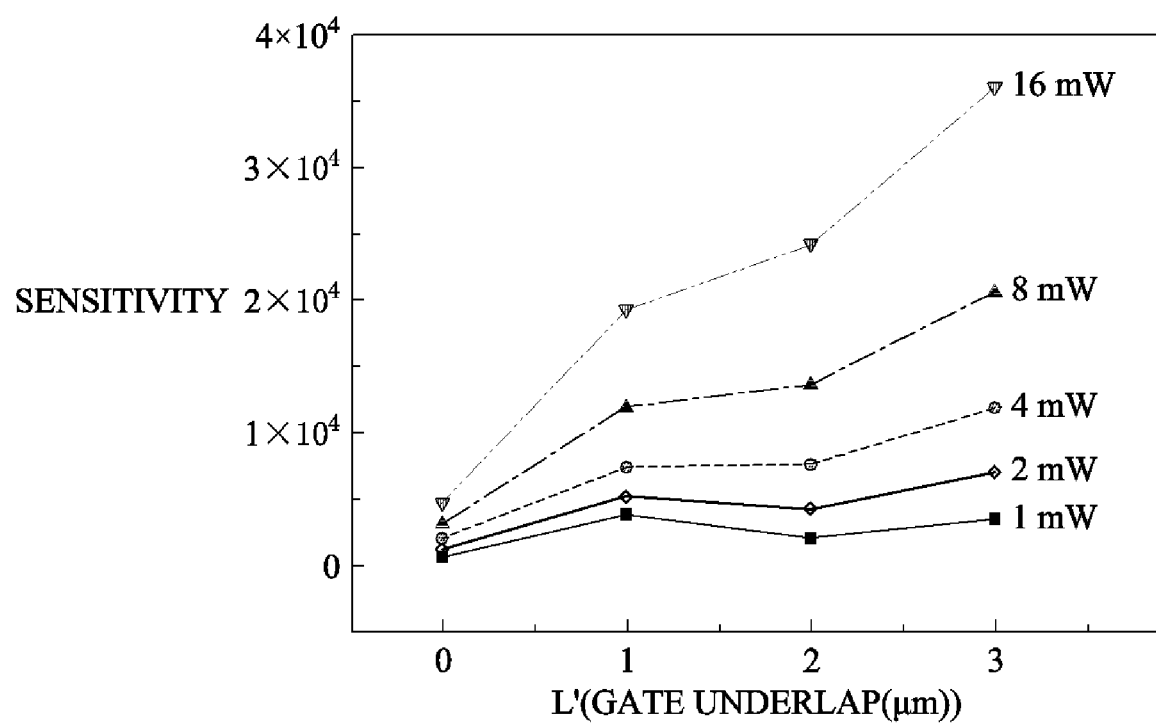
FIG. 11 is a graph showing sensitivity according to the non-overlapping length of a light amplification phototransistor according to an embodiment of the present invention.

FIG. 11 is a graph showing sensitivity according to the non-overlapping length of a light amplification phototransistor according to an embodiment of the present invention.

Referring to FIG. 11, it can be seen that, as non-overlapping length and photoreactivity increase, sensitivity increases. Therefore, since the device for measuring biological information including a sensor array according to an embodiment of the present invention includes non-overlapping regions, sensors included in the device may amplify optical gain and photoreactivity.

Figure 12:
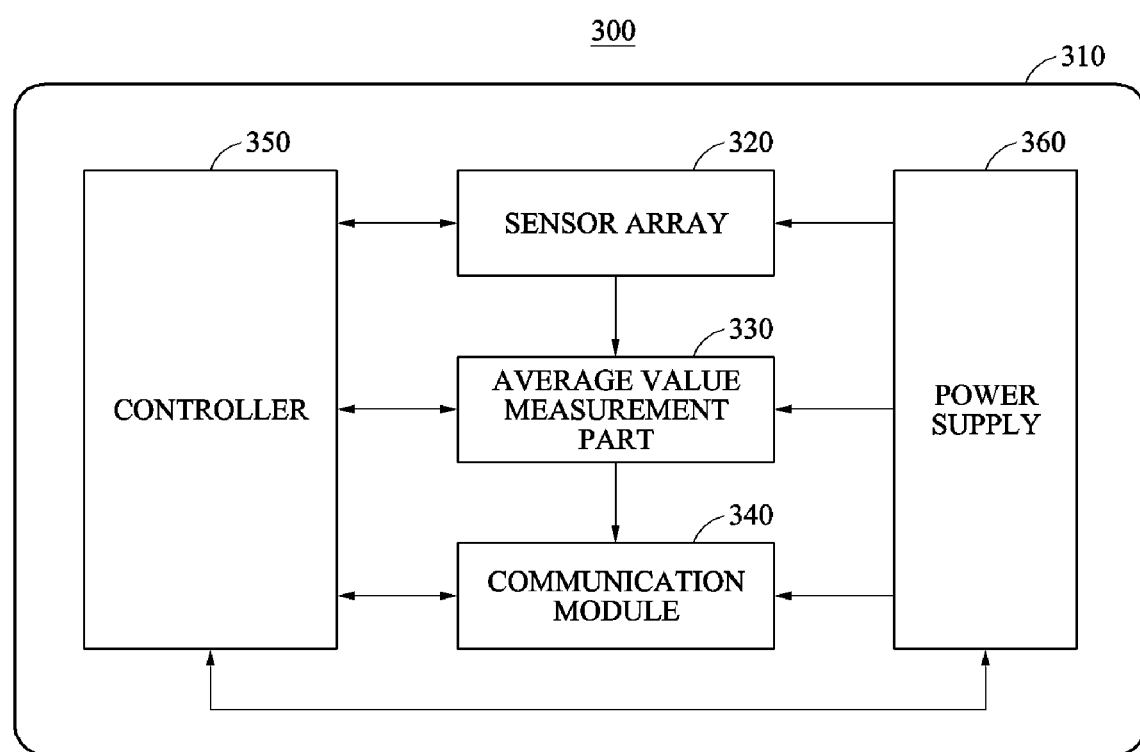
FIG. 12 is a block diagram for explaining a configuration of a device for measuring biological information including a sensor array according to another embodiment of the present invention.

FIG. 12 is a block diagram for explaining a configuration of a device for measuring biological information including a sensor array according to another embodiment of the present invention.

Referring to FIG. 12, in a device for measuring biological information including a sensor array 300 according to another embodiment of the present invention, the resistance values of a measurement target site (e.g., the skin tissues) are measured by a sensor array 320 formed on a substrate 310, and an average value of biological information is measured based on the measured resistance values.

The device for measuring biological information including a sensor array 300 according to another embodiment of the present invention includes the sensor array 120 and the average value measurement part 130.

Herein, the substrate 310 may include a plurality of electrically conductive sensors. For example, the substrate 310 may be formed of at least one of paper, a polymer, woven fabric, and insulated metal foil.

According to one embodiment, the substrate 310 may be a flexible substrate that can be attached to the skin, and may be composed of at least one of polyimide, polycarbonate, polyacrylate, polyetherimide, polyethersulfone, polyethylene terephthalate, and polyethylene naphthalate.

The sensor array 320 includes a plurality of sensors forming an island network, in which nodes and a plurality of multi-channels are connected, and is formed on the substrate 310.

For example, the sensor array 320 may include multi-channels formed of a plurality of channels, and the multi-channels may be formed in a meander pattern having a meandering shape to cover a relatively large area.

According to one embodiment, the multi-channels may be formed of at least one of a meander pattern with spiral and rectangular shaped loops, a pair of intermeshed meander patterns, a pair of independent concentric circular patterns in which an inner helix is formed in an outer helix, a pair of intermeshed circular patterns, a meander pattern in which a small rectangular loop is formed in a large loop, a meander pattern in which a small circular or oval circular loop is formed in a large loop, and a series of helical patterns with a common central axis. The patterns of the above-described types may be arranged in a matrix form and connected in series or parallel, and thus the present invention is not limited to the pattern forms.

In addition, the sensor array 320 may include sensors forming an island network including a plurality of multi-channels connected to each other via a node and including terminals.

For example, the island network may have a '∩' shape in which four multi-channels are connected to each other in series via nodes, wherein terminals are connected at each end of the '∩' shape.

According to one embodiment, the multi-channels may be formed in a '∩' shape that is inclined at an angle of at least one of 0°, 90°, 180°, and 270°, and may be connected in parallel via nodes, or may be connected in series and in parallel via nodes.

In addition, the island network may be formed of one or more multi-channels. When the island network is formed, at least one of a connection manner (serial or parallel), the pattern of multi-channels, the number of multi-channels, node number, and terminal number may be changed according to embodiments. Thus, the present invention is not limited to the above-described manner.

According to one embodiment, multi-channels formed of a platinum (Pt) thin film on a film made of a polyimide solution are patterned through a photolithography process, and then the patterned multi-channels are transferred to the substrate 310 to form the sensor array 320 according to another embodiment of the present invention.

In addition, a conductive layer including platinum may be formed on a film made of a polyimide solution, and then patterning and etching may be performed through a photolithography process to form the multi-channels. The conductive layer may be formed on a film by sputtering deposition, electron beam (E-beam) technology, and evaporation.

In addition, the multi-channels may be formed using at least one resistor of gold (Au), tungsten (W), palladium (Pd), silicon (Si), silicon alloys, and conductive metal oxides.

The sensor array 320 may be connected to an IC circuit formed on the substrate 310 and formed in a patch-like structure.

The IC circuit is capable of performing signal filtering, amplification, digitization, and integrated processing. According to one embodiment, the IC circuit may be a multi-functional integrated circuit sensor that processes signals in the substrate 310.

In addition, the patch-like structure may be implemented in various sizes and shapes depending on the area and the characteristics of an attachment site on the body surface, and may include a medical grade skin contact adhesive suitable for application to the skin. Also, the patch-like structure may have at least one of circular, square, rectangular, rhombic, cruciform, curved, and X-shaped shapes having various sizes.

An average value measurement part 330 measures an average value for the sensor array 320 based on resistance values measured by terminals.

The average value measurement part 330 may measure an average value of biological information based on resistance values of the skin tissues measured by each terminal.

Herein, the biological information may include at least one of heart rate (pulse), oxygen saturation, and temperature.

According to one embodiment, the average value measurement part 330 may measure an integrated average value for different regions (areas) based on resistance values received from the sensor arrays 320 attached to different skin tissues.

The device for measuring biological information including a sensor array 300 according to another embodiment of the present invention may further include a communication module 340, a controller 350, and a power supply 360.

The communication module 340 may transmit the measured average value of biological information from the average value measurement part 330 to the outside.

The communication module 340 may transmit and receive an average value with transmission bandwidths. According to coverage, at least one of ZigBee, Bluetooth, GeoWave, and Wi-Fi may be applied to the communication module 340.

In addition, values of biological information measured using the device for measuring biological information including a sensor array 300 according to another embodiment of the present invention may be transmitted to at least one of a user terminal, an integrated server, a healthcare institution, and an external temperature sensing device.

According to one embodiment, an average value measured by the device for measuring biological information including a sensor array 300 according to another embodiment of the present invention may be transmitted to an integrated server, and a user may receive health-related information from the integrated server, thereby receiving continuous healthcare services. The health status of a user may be analyzed in real time based on biological information measured in real time, and the user may receive the preventive and prescription services from a hospital and a health management institution (health center).

In addition, the integrated server may comprehensively manage an average value of biological information received from the device for measuring biological information including a sensor array 300 according to another embodiment of the present invention, and may provide a user, manager, and hospital personnel with information on changes in biological information and health status.

The controller 350 may control an average value of biological information to be measured based on resistance values measured by at least one sensor selected in response to a control command received from the communication module 340.

For example, the controller 350 may perform control so that the average value measurement part 330 measures an average value of biological information using resistance values measured by sensors located at specific regions among matrix-type sensors included in the sensor array 320 and arranged in series and parallel in response to a control command received from the outside.

In addition, according to one embodiment, the controller 350 may be disposed on the substrate 310, but may be located outside the substrate 310 to control at least one of the sensor array 320, the average value measurement part 330, the communication module 340, and the power supply 360.

The power supply 360 may supply driving power to at least one of the sensor array 320, the average value measurement part 330, the communication module 340, and the controller 350.

For example, the power supply 360 may be composed of an active element using an ultra-small rechargeable battery or an ultra-small super-capacitor.

According to one embodiment, the power supply 360 may be a primary cell such as a coin cell or a secondary cell such as a lithium polymer battery. When the power supply 360 is a secondary cell, the power supply 360 may be charged by an external power source. When the power supply 360 is a primary cell such as a coin cell, the power supply 360 may be replaced with a new one.

The device for measuring biological information including a sensor array 300 according to another embodiment of the present invention may further include a selection switch (not shown). Hereinafter, the selection switch will be described in detail with reference to FIG. 21.

Figure 21:
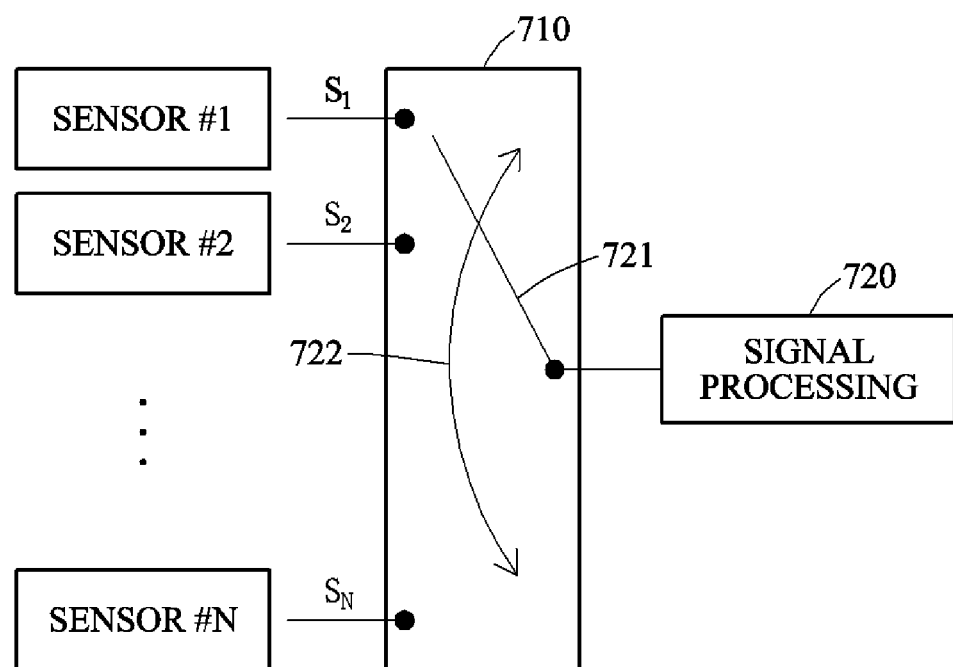
FIG. 21 illustrates an operation example of a selection switch included in a device for measuring biological information including a sensor array according to another embodiment of the present invention.

FIG. 21 illustrates an operation example of a selection switch included in a device for measuring biological information including a sensor array according to another embodiment of the present invention.

Referring to FIG. 21, a selection switch 710 according to another embodiment of the present invention includes a sensor selection module 721 capable of selecting any sensors from among a plurality of sensors (sensors #1, #2, . . . , and #N), and a signal processor 720 is capable of sensing resistance values ($DS_1$, $DS_2$, . . . , and $DS_N$) measured by each of any sensors in response to a control command transmitted from the controller 350.

In addition, in the device for measuring biological information including a sensor array 300 according to another embodiment of the present invention, any sensors from among a plurality of sensors may be selected using the signal processor 720, and a method of measuring resistance values for biological information measured by the selected sensors may be configured in the form of a switch as shown in FIG. 21.

According to one embodiment, the signal processor 720 may be the average value measurement part 330 of the device for measuring biological information including a sensor array 300 according to another embodiment of the present invention.

Figure 13:
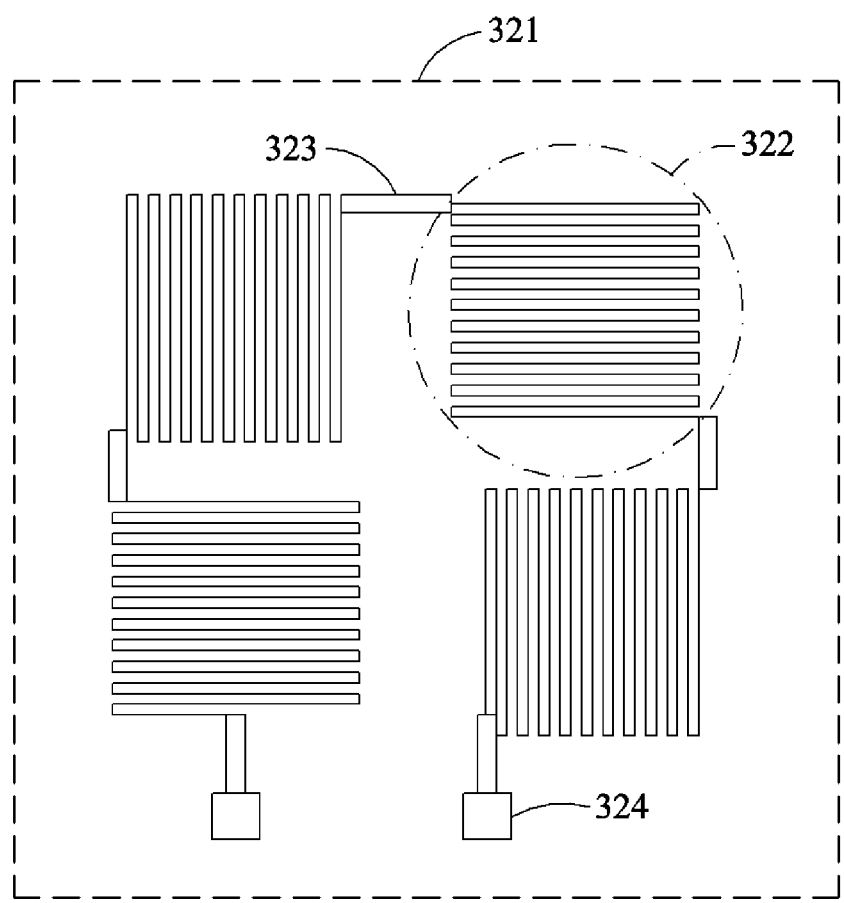
FIG. 13 is a schematic top view of a sensor according to another embodiment of the present invention.

FIG. 13 is a schematic top view of a sensor according to another embodiment of the present invention.

Referring to FIG. 13, a sensor 321 according to another embodiment of the present invention is composed of a plurality of multi-channels 322 connected to each other via nodes 323, and includes terminals 324 for measuring resistance values for biological information of the skin tissues.

As shown in FIG. 13, the multi-channels 322 of the sensor 321 may be connected to each other via each of the nodes 323, and the terminals 324 may be connected to the multi-channels 322 located at both ends.

The multi-channels 322 may be connected to each other via the nodes 323 in series, and the multi-channels 322 connected to each other via the nodes 323 may form an island shape.

The island shape is formed in a 2×2 structure using the multi-channels 322 having a length-to-width ratio of less than 100. Therefore, the multi-channels 322 formed in the island shape may detect the temperature of a wide area (large area) of the skin to be measured, as compared with linear multi-channels.

In addition, the multi-channels 322 may be formed in a meander pattern having a meandering shape to cover a relatively large area, and may be formed at an angle of at least one of 0°, 90°, 45°, −45°, and −90°.

For example, the multi-channels 322 may be formed to be inclined at an angle of at least one of 0°, 90°, 45°, −45°, and −90° to minimize a change in resistance due to expansion and contraction of the skin.

According to one embodiment, the multi-channels 322 may be formed of at least one of a meander pattern with spiral and rectangular shaped loops, a pair of intermeshed meander patterns, a pair of independent concentric circular patterns in which an inner helix is formed in an outer helix, a pair of intermeshed circular patterns, a meander pattern in which a small rectangular loop is formed in a large loop, a meander pattern in which a small circular or oval circular loop is formed in a large loop, and a series of helical patterns with a common central axis. The patterns of the above-described types may be arranged in a matrix form and connected in series or parallel, and thus the present invention is not limited to the pattern forms.

In addition, each of the multi-channels 322 may be a negative temperature coefficient thermistor.

For example, a printed negative temperature coefficient (NTC) thermistor may be used as the multi-channels 322, without being limited thereto. The multi-channels 322 are equally applicable as any flexible temperature sensor in which resistance varies depending on temperature, and may be formed of at least one of a positive temperature coefficient (PTC) thermistor, a resistance temperature device (RTD), and any device manufactured on a flexible substrate material.

In addition, each of the multi-channels 322 may have a length-to-width ratio of less than 100. That is, since each of the multi-channels 322 has a length-to-width ratio of less than 100, when patterning is performed through a photolithography process, the problem of breaking of the multi-channels may be solved.

Resistance applied to the nodes 323 adjacent to any two of the multi-channels 322 according to another embodiment of the present invention is constant, and may be equal to the resistance of any one of the multi-channels 322. In addition, the temperature relevance of resistance between the nodes 323 may be the same as the temperature relevance of each of the multi-channels 322.

In addition, the terminals 324 constituting the sensor 321 of a device for measuring biological information including a sensor array according to another embodiment of the present invention may measure resistance values for an object (a measurement target site or the skin tissues).

According to one embodiment, the terminals 324 may be formed in each of the sensors 321, and may be configured within the sensor array 320 composed of a plurality of the sensors 321 to measure resistance values in the sensor array 320.

Referring again to FIG. 13, the number of the multi-channels 322 constituting the sensor 321 is four. However, at least one of the shape and number of the multi-channels 322, the number of the nodes 323, and the number of the terminals 324 may vary according to embodiments of the present invention. Thus, the present invention is not limited thereto.

Hereinafter, the sensor array 320 including the sensors 321 will be described in detail with reference to FIGS. 14A to 14E.

FIGS. 14A to 14E include views for explaining sensor arrays according to various embodiments of the present invention.

Figure 14A:
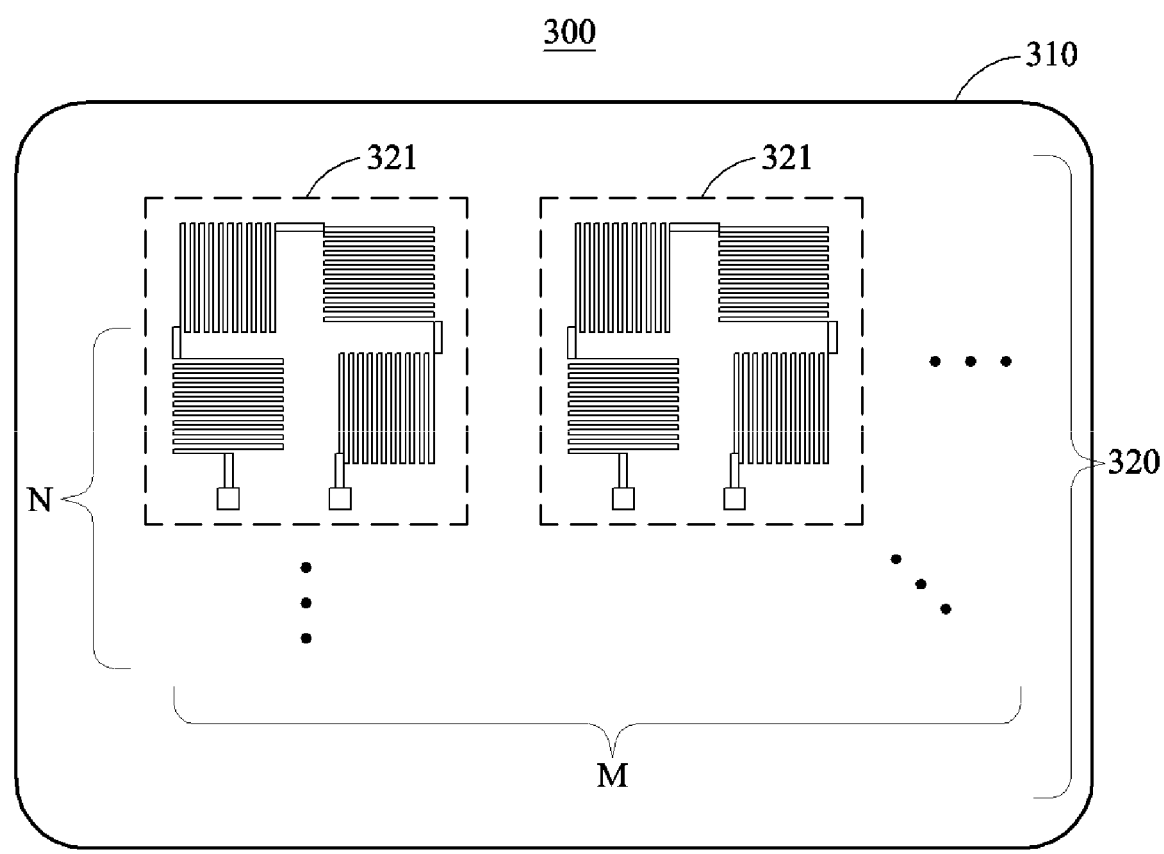
FIGS. 14A to 14E include views for explaining sensor arrays according to various embodiments of the present invention.

Referring to FIG. 14A, the device for measuring biological information including a sensor array 300 according to another embodiment of the present invention may include the sensor array 320 composed of the sensors 321 arranged in a matrix form of N×M and formed in series and parallel on the substrate 310.

The device for measuring biological information including a sensor array 300 according to another embodiment of the present invention illustrated in FIG. 14A is formed in the form of the sensor 321 as described in FIG. 13, and the number and arrangement of the sensors 321 may be arbitrarily determined according to embodiments of the present invention.

According to one embodiment, in the sensor array 320, the sensors 321 may be connected in series or in parallel, or may be formed in a combination of series and parallel.

Figure 14B:
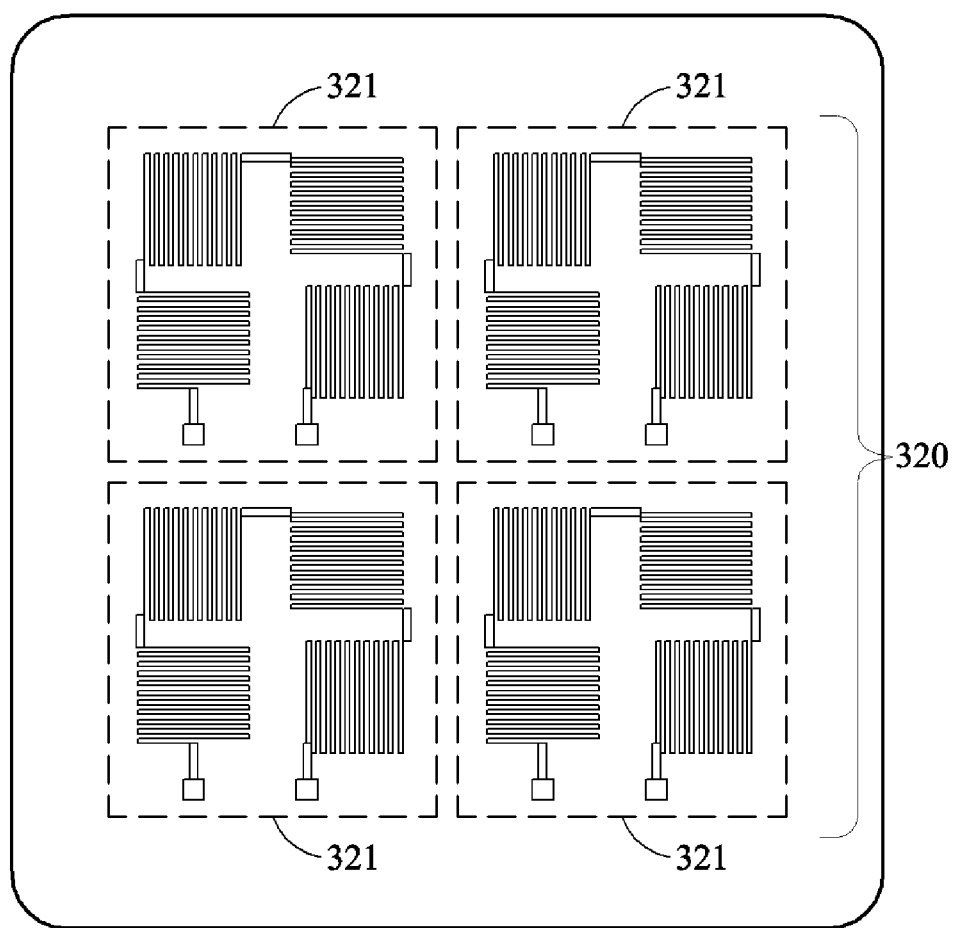

Referring to FIG. 14B, the device for measuring biological information including a sensor array 300 according to another embodiment of the present invention may include the sensor array 320 composed of the four sensors 321 arranged in a matrix form of 2×2 on the substrate 310. The four sensors 321 may be formed as described in FIG. 13.

Figure 14C:
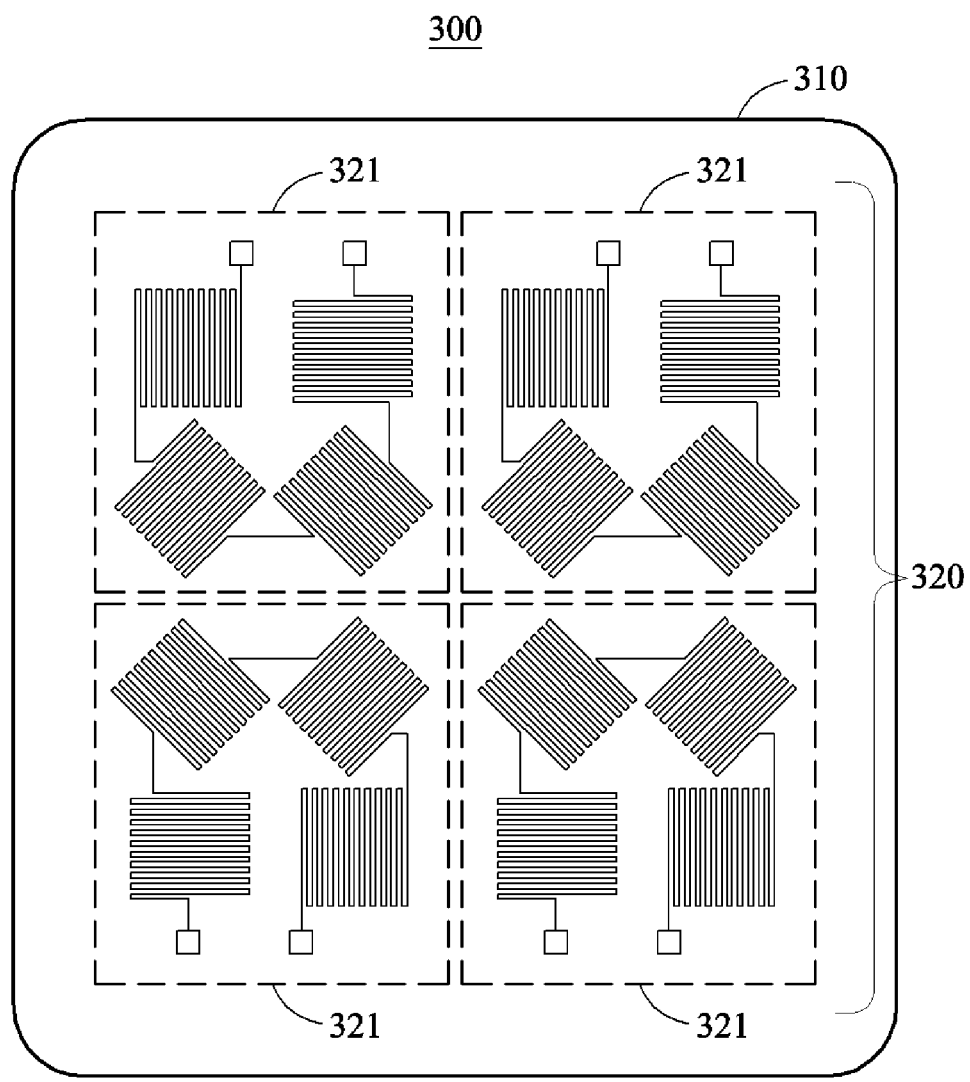

Referring to FIG. 14C, the device for measuring biological information including a sensor array 300 according to another embodiment of the present invention may include the sensor array 320 composed of the four sensors 321 arranged in a matrix form of 2×2 on the substrate 310. Herein, each of the sensors 321 may represent different forms.

For example, in the two sensors 321 formed on the upper portion of a device for measuring biological information including a sensor array 300, four multi-channels connected to each other via nodes are formed in a '∪' shape, wherein terminals are connected to each end of the '∪' shape. In the two sensors 321 formed on the lower portion of the device, four multi-channels connected to each other via nodes are formed in a '∩' shape, wherein terminals are connected to each end of the '∩' shape.

In addition, each of multi-channels constituting the sensor 321 may be formed to be inclined at an angle of at least one of 0°, 90°, 45°, −45°, and −90°, but the angle of the multi-channels is not limited thereto.

That is, the device for measuring biological information including a sensor array 300 according to another embodiment of the present invention may include the sensors 321 including multi-channels modified according to an embodiment of the present invention to minimize a change in resistance depending on measurement target sites. The structure and shape of the sensors 321 and the angle, shape, and number of multi-channels constituting the sensors 321 are not limited.

Figure 14D:
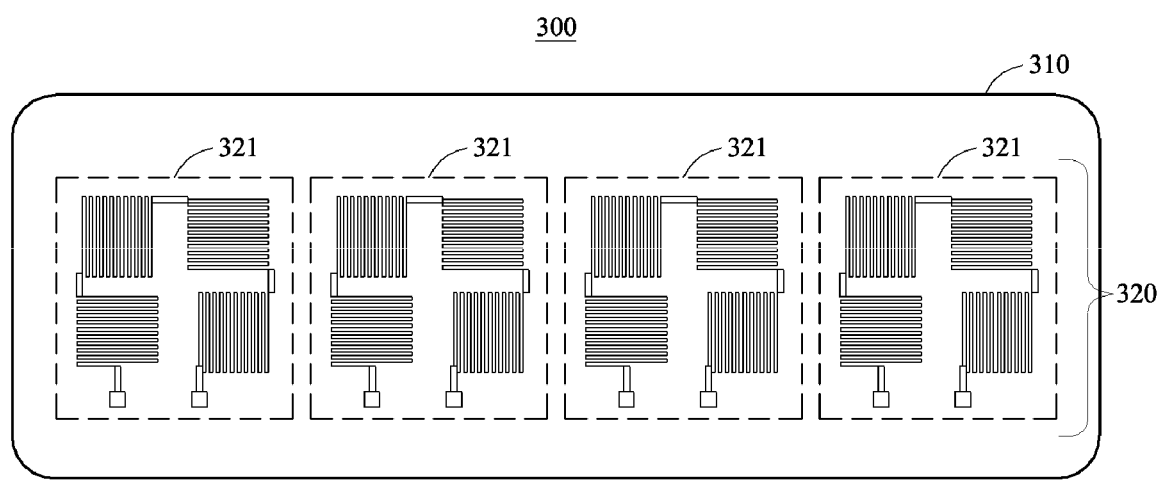

Referring to FIG. 14D, the device for measuring biological information including a sensor array 300 according to another embodiment of the present invention may include the sensor array 320 composed of the four sensors 321 arranged in a matrix form of 1×4 on the substrate 310. The sensors 321 may be formed as described in FIG. 13.

Figure 14E:
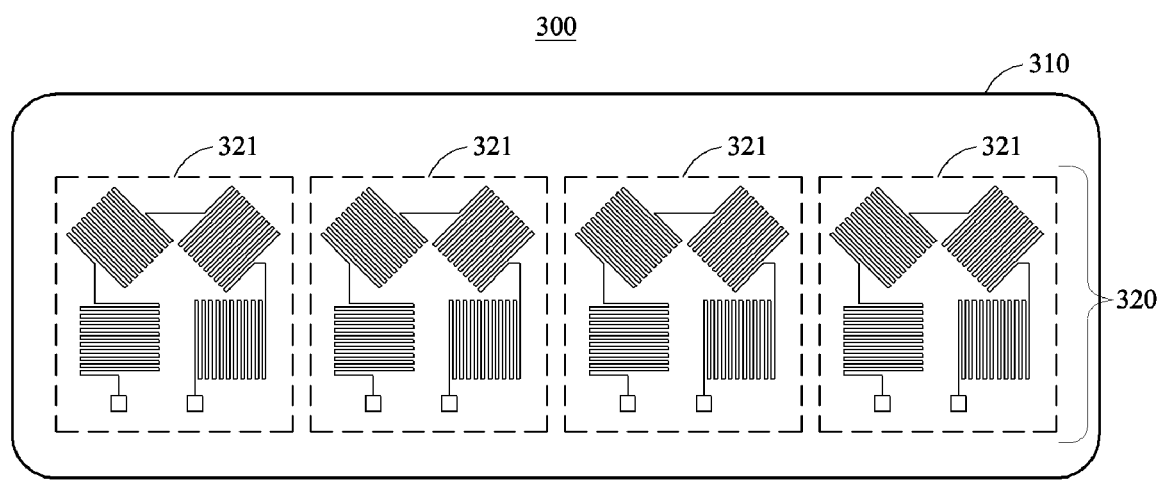

Referring to FIG. 14E, the device for measuring biological information including a sensor array 300 according to another embodiment of the present invention may include the sensor array 320 composed of the four sensors 321 arranged in a matrix form of 1×4 on the substrate 310.

Herein, in the four sensors 321, four multi-channels connected to each other via nodes are formed in a '∩' shape, wherein terminals are connected to each end of the '∩' shape. Each of multi-channels constituting the four sensors 321 may be formed to be inclined at an angle of at least one of 0°, 90°, 45°, −45°, and −90°.

As shown in FIGS. 14B to 14E, the device for measuring biological information including a sensor array 300 including the four sensors 321 may measure the same total resistance value from the sensor array 320.

Herein, the total resistance value of the sensor array 320 may be calculated by Equation 1 below.

$$R_t = \rho_t \times \ell / A,  \quad \text{[Equation 1]}$$

wherein $R_t$ represents a resistance value, $\rho_t$ represents specific resistance, $\ell$ represents length, and A represents a cross section.

The device for measuring biological information 300 including the sensor array 320 composed of the sensors 321 illustrated in FIGS. 14B to 14E exhibits a specific resistance value of $1.1 \times 10^{-7}$ and a cross section of 50 um×50 um at 20° C., and thus may constantly exhibit a total resistance value of 10,000Ω.

In addition, the device for measuring biological information including a sensor array 300 according to another embodiment of the present invention may include at least one of the average value measurement part 330, the communication module 340, the controller 350, the power supply 360, and a selection switch (not shown) on the substrate 310 in addition to the sensor array 320 illustrated in FIGS. 14A to 14E.

Figure 15A:
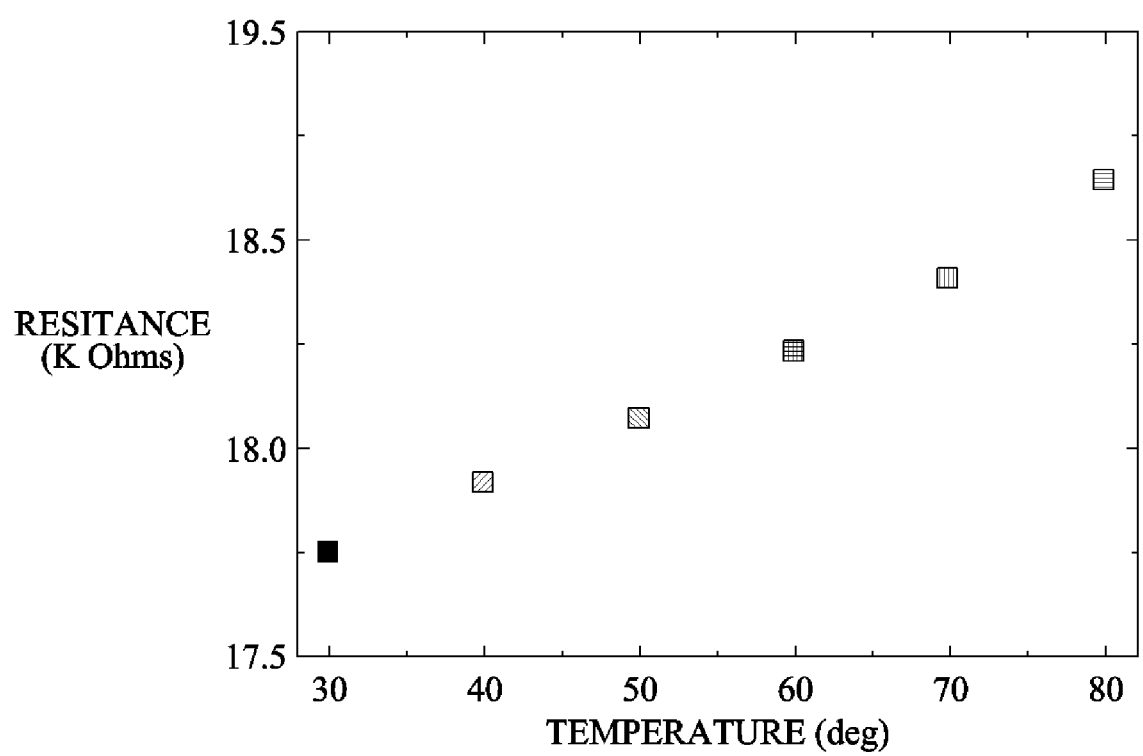
FIGS. 15A and 15B include graphs showing resistance values measured by a device for measuring biological information including a single sensor according to another embodiment of the present invention depending on temperature change.
Figure 15B:
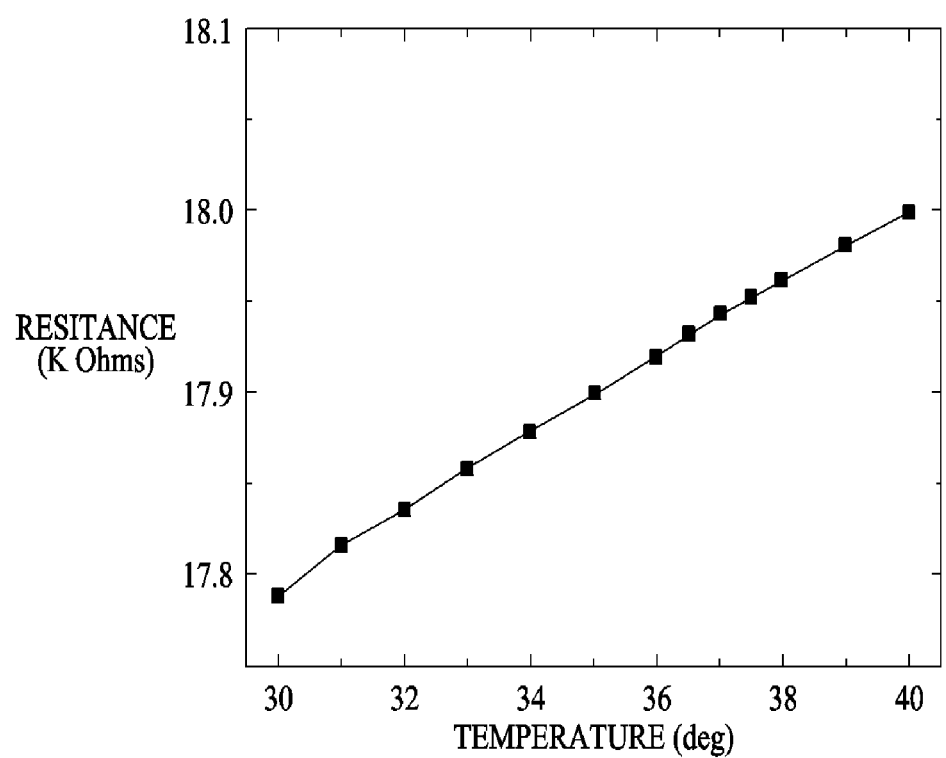

FIGS. 15A and 15B include graphs showing resistance values measured by a device for measuring biological information including a single sensor according to another embodiment of the present invention depending on temperature change.

FIG. 15A is a graph showing resistance values for an object measured using a device for measuring biological information including a single sensor, wherein the resistance values are measured at 10° C. intervals from 30° C. to 80° C. FIG. 15B is a graph showing resistance values for an object measured using a device for measuring biological information including a single sensor, wherein the resistance values are measured at 1° C. intervals from 30° C. to 40° C. and at 0.5° C. intervals from 36° C. to 38° C.

As shown in FIGS. 15A and 15B, in the case of a device for measuring biological information including a single sensor, the measured temperature changes depending on the position and area of the sensor attached to the object. Therefore, the device is limited in accurately measuring the temperature of the object to be measured.

Figure 16A:
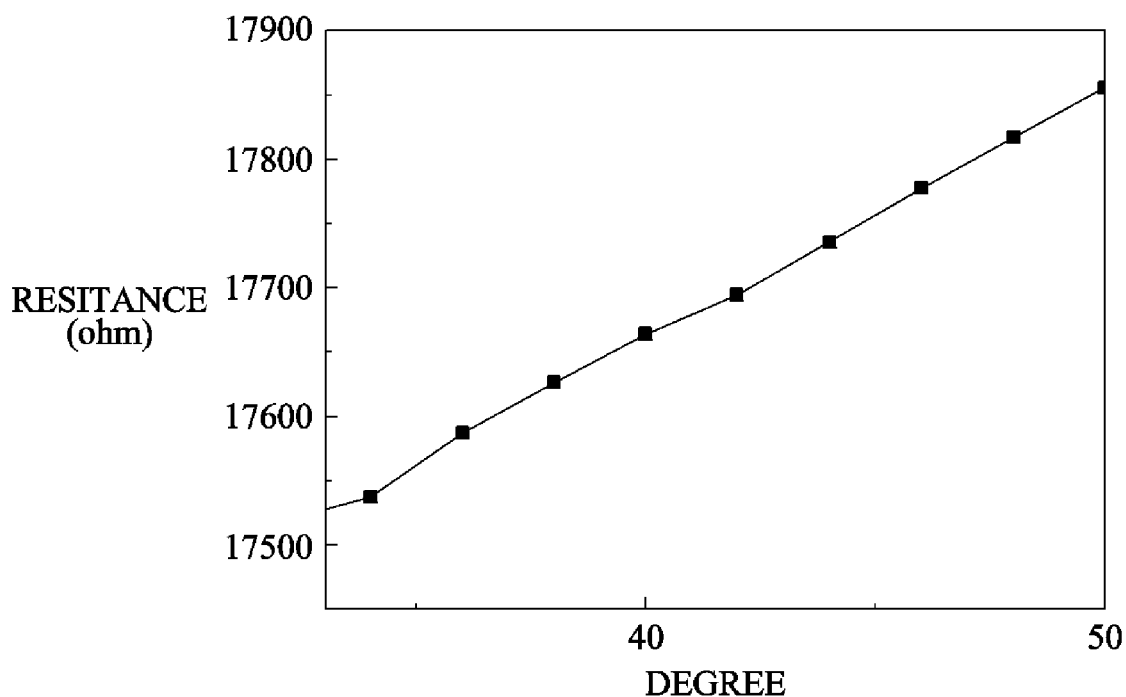
FIGS. 16A and 16B include graphs showing the average values of a device for measuring biological information including a sensor array according to another embodiment of the present invention depending on temperature change.
Figure 16B:
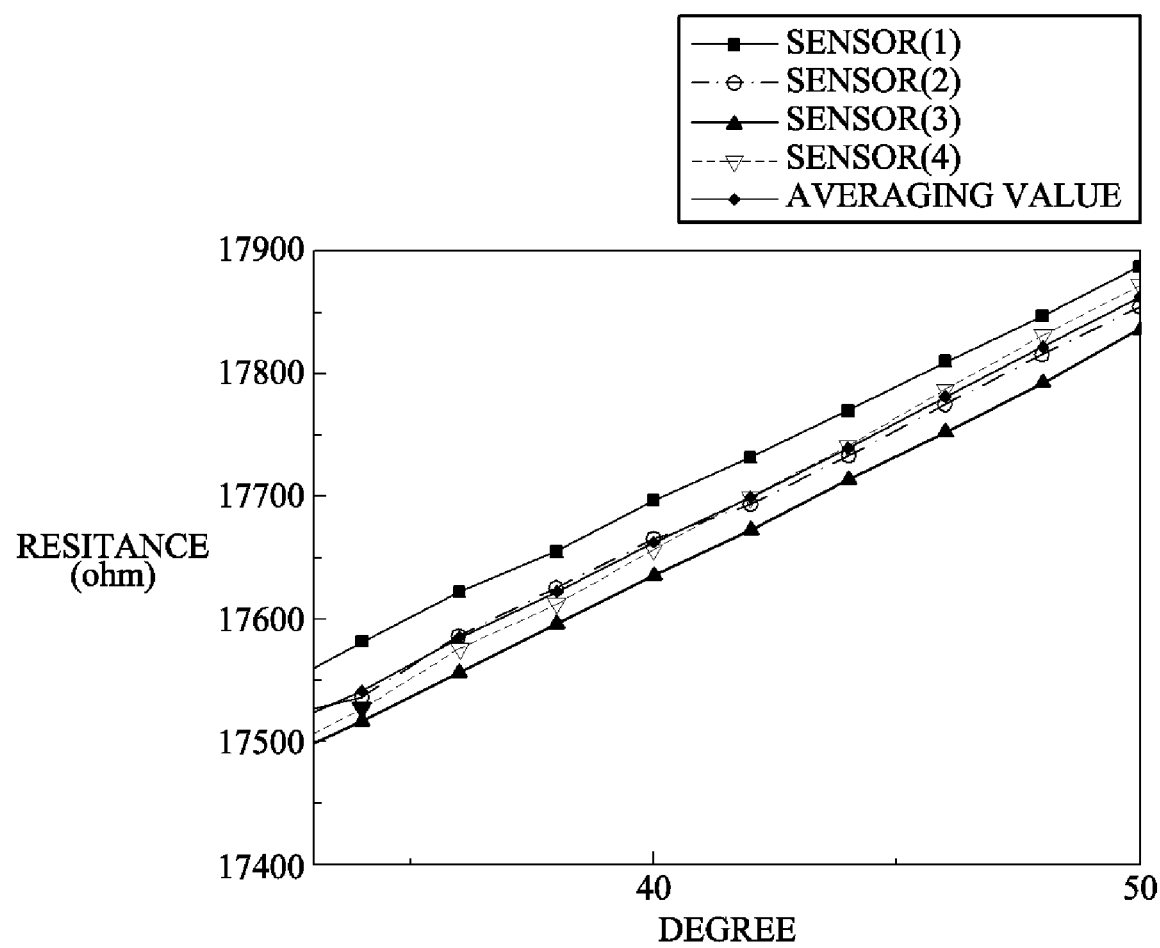

FIGS. 16A and 16B include graphs showing the average values of a device for measuring biological information including a sensor array according to another embodiment of the present invention depending on temperature change.

FIG. 16A is a graph showing resistance values for an object depending on temperature change measured using a device for measuring biological information including a single sensor. FIG. 16B is a graph showing resistance values for an object depending on temperature change measured using a device for measuring biological information including a sensor array including four sensors.

Referring to FIGS. 16A and 16B, compared with a device for measuring biological information including a single sensor, when a device for measuring biological information including a sensor array composed of four sensors is used, the reliability of the average value of biological information is higher.

Figure 17:
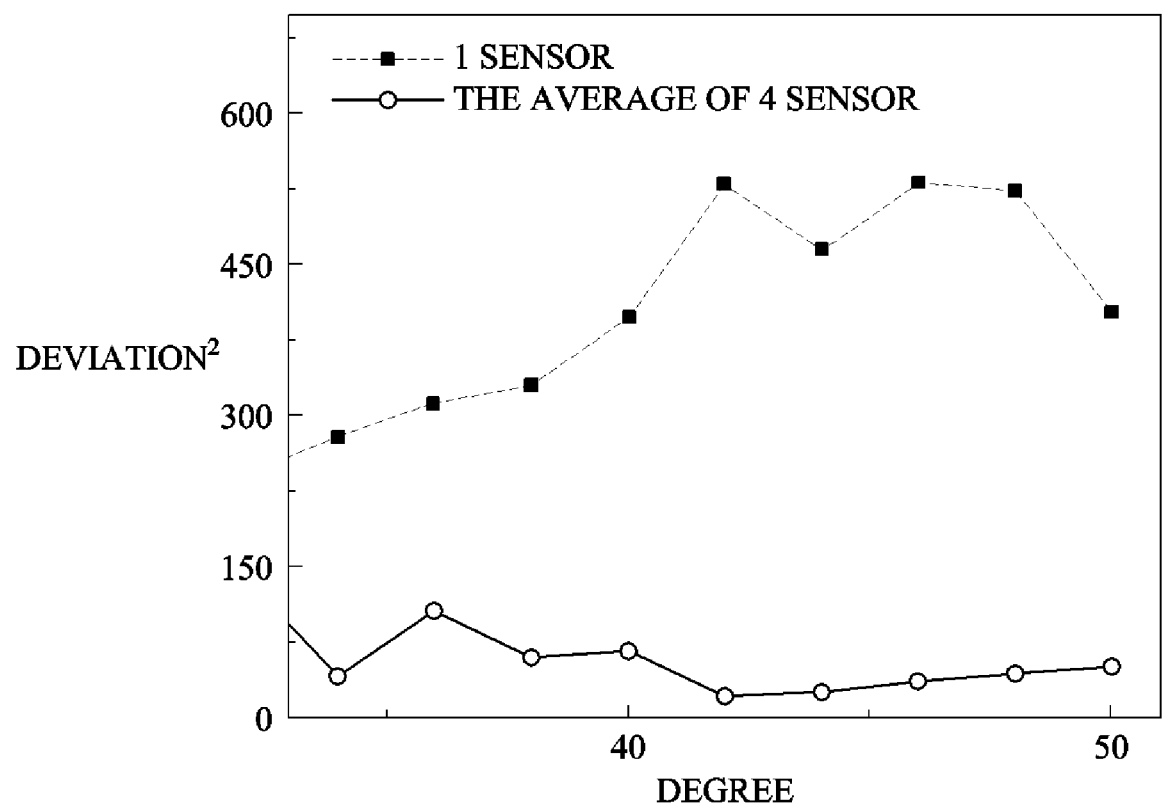
FIG. 17 is a graph showing the deviations of a device for measuring biological information including a sensor array according to another embodiment of the present invention depending on temperature change.

FIG. 17 is a graph showing the deviations of a device for measuring biological information including a sensor array according to another embodiment of the present invention depending on temperature change.

More specifically, FIG. 17 is a graph showing the deviations of a device for measuring biological information including a single sensor or a device for measuring biological information including a sensor array including four sensors depending on temperature change from 0° C. to 50° C.

Referring to FIG. 17, it can be confirmed that a device for measuring biological information including a sensor array composed of four sensors, wherein the device measures average temperature based on resistance values measured by four sensors, has a smaller deviation than a device for measuring biological information including a single sensor.

That is, in the case of a device for measuring biological information including a sensor array composed of a plurality of sensors, since error caused by external factors is small in average temperature measurement, temperature for an object may be accurately and constantly measured.

Figure 18:
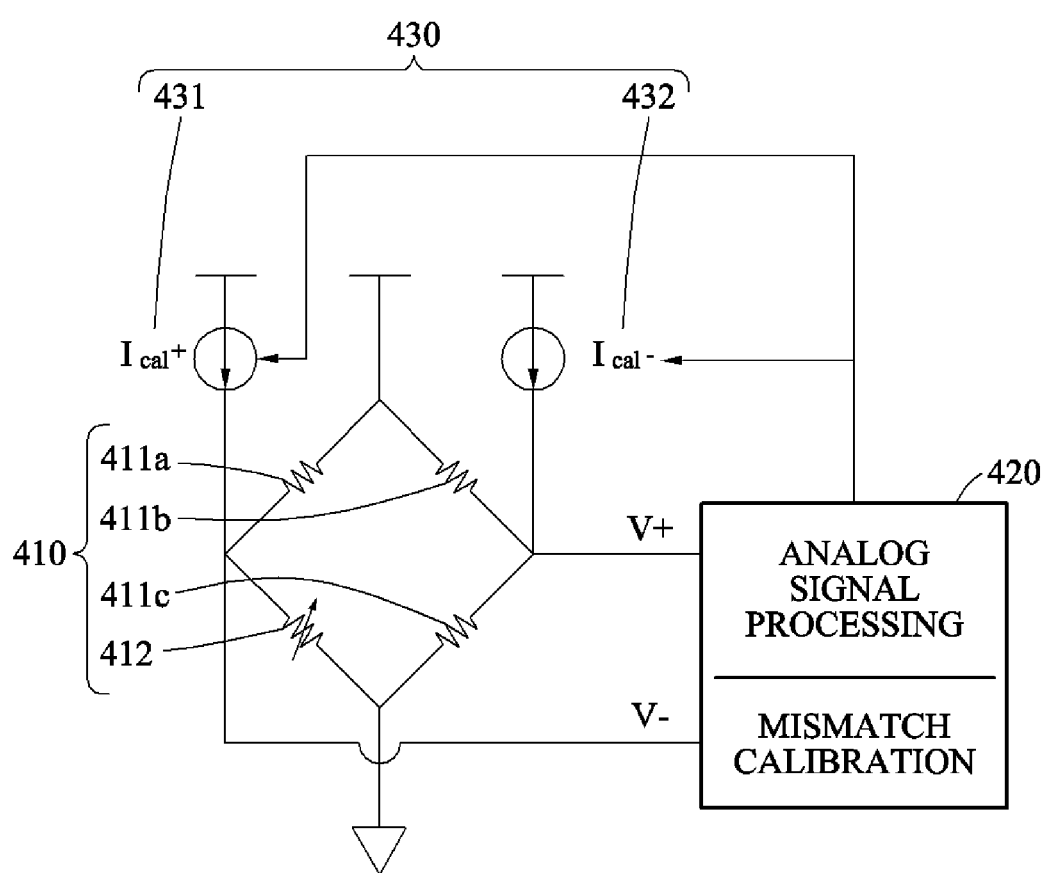
FIG. 18 is a conceptual diagram for explaining a sensor applied to a device for measuring biological information including a sensor array according to another embodiment of the present invention.

FIG. 18 is a conceptual diagram for explaining a sensor applied to a device for measuring biological information including a sensor array according to another embodiment of the present invention.

Referring to FIG. 18, the sensor 321 may include bridge circuits 410 and a signal processor 420.

The bridge circuits 410 may include a plurality of resistance elements 411 having a specific resistance value and a temperature sensing element 412 having a variable resistance value. For example, the bridge circuits 410 may be implemented as a Wheatstone bridge to precisely measure the resistance values of the temperature sensing element. More specifically, one end (corresponding to a node between a first resistance element 411a and the temperature sensing element 412) and the other end (corresponding to a node between second and third resistance elements 411b and 411c) of the bridge circuits 410 may be connected to both input ends of the signal processor 420. The bridge circuits 410 may provide voltage to both input ends of the signal processor 420 in accordance with changes in the resistance values of the temperature sensing element 412.

In an embodiment, the temperature sensing element 412 may be implemented through a variable resistance element, the resistance value of which changes in accordance with temperature change of an object. For example, the temperature sensing element 412 may be implemented as a platinum resistance or a copper resistance to sense a temperature change in an object.

The signal processor 420 may determine whether offset voltage is generated based on voltage applied from the bridge circuits 410. More specifically, the signal processor 420 may detect changes in the resistance values of the temperature sensing element 412 based on voltage applied from the bridge circuits 410 and provide additional current 430 to both ends of the bridge circuits 410. For example, the first additional current 431 may be provided at one end of the bridge circuits 410 and the second additional current 432 may be provided at the other end of the bridge circuits 410, so that offset voltage output from the bridge circuits 410 may be removed. That is, the signal processor 420 may perform calibration by providing the additional current 430 to both ends of the bridge circuits 410. In this case, the amount of the additional current provided to the bridge circuits 410 may be determined depending on the magnitude of offset voltage. Once calibration is performed and offset voltage is removed, the signal processor 420 may sense temperature based on the resistance value of the temperature sensing element 412.

Figure 19:
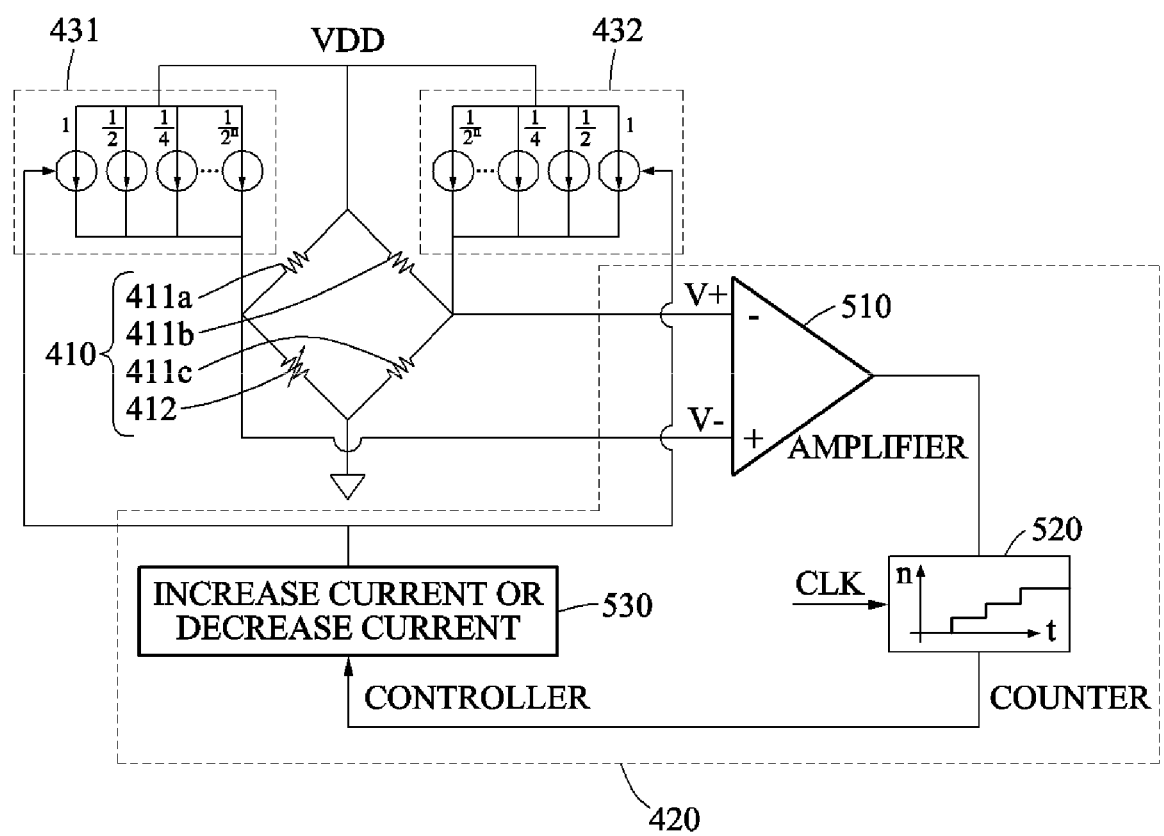
FIG. 19 is a circuit diagram of a sensor applied to a device for measuring biological information including a sensor array according to another embodiment of the present invention.

FIG. 19 is a circuit diagram of a sensor applied to a device for measuring biological information including a sensor array according to another embodiment of the present invention.

Referring to FIG. 19, the sensor 321 may include the bridge circuits 410 and the signal processor 420, and the signal processor 420 may include an amplifier 510, a counter 520, and a controller 530.

The amplifier 510 may receive output voltage loaded at both ends of the bridge circuits 410. More specifically, output voltage generated in both ends of the bridge circuits 410 (V−, V+) may be applied to both input ends of the amplifier 510, and the controller 530 may determine whether offset voltage is generated based on difference values of the output voltage (V−, V+). When offset voltage is generated, the controller 530 may provide the additional current 43 1and 432 to both ends of the bridge circuits 410. Then, the bridge circuits 410 may provide the changed output voltage again to the amplifier 510 based on the additional current 431 and 432.

The controller 530 may determine the values of the additional current 431 and 432 to be applied to the bridge circuits 410 based on the offset voltage value. For example, the controller 530 may additionally apply positive current to increase output voltage (V−) loaded at one end of the bridge circuits 410, and may additionally apply negative current to reduce output voltage (V+) loaded at the other end of the bridge circuits 410. That is, the controller 530 may minimize offset voltage by adjusting the values of the additional current 431 and 432.

In an embodiment, the sensor array may determine the presence or absence of offset voltage in response to changes in the resistance values of the temperature sensing element 412 of the sensor 321 at specific intervals, and may repeat calibration stepwise until offset voltage is removed. More specifically, the counter 520 may generate a clock (CLK) and provide the same to the controller 530, and the controller 530 may determine whether offset voltage is generated based on the period of the clock (CLK).

For example, when offset voltage is generated in the first period of the clock (CLK), the controller 530 may apply the additional current 431 and 432 to the bridge circuits 410 to reduce the offset voltage. The controller 530 may determine whether offset voltage again occurs in the second period of the clock (CLK). When offset voltage is still present, the controller 530 may again provide the additional current 431 and 432 to both ends of the bridge circuits 410.

The controller 530 may repeat the above process until offset voltage is removed, and perform temperature detection when removal of offset voltage is completed.

Figure 20:
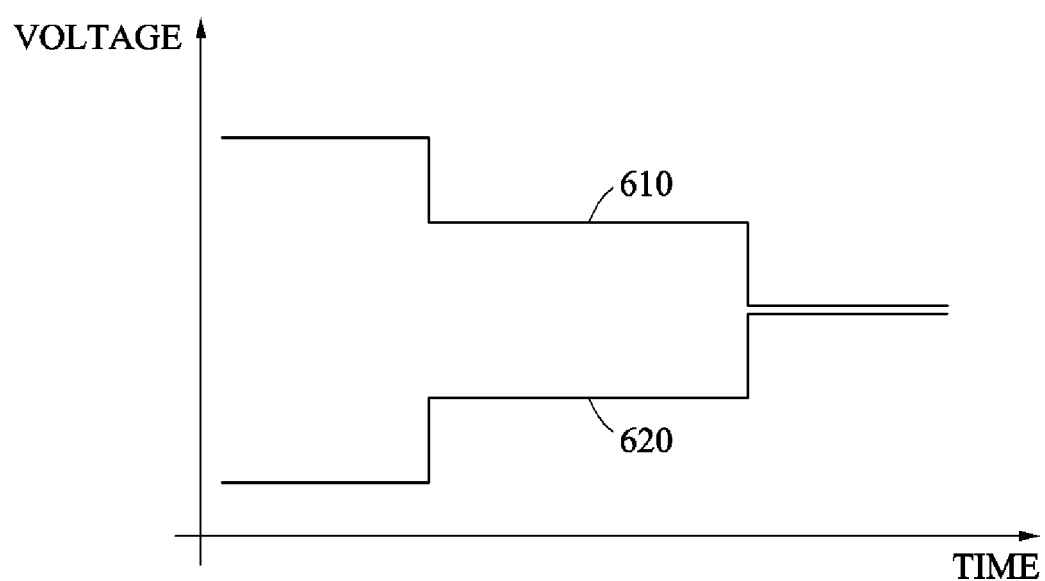
FIG. 20 is a graph showing a process of removing offset voltage performed by a device for measuring biological information including a sensor array according to another embodiment of the present invention.

FIG. 20 is a graph showing a process of removing offset voltage performed by a device for measuring biological information including a sensor array according to another embodiment of the present invention.

Referring to FIG. 20, offset voltage generated based on difference values of the output voltages 610 and 620 of the bridge circuits 410 may be removed by applying additional current. In this case, when the first output voltage 610 is assumed to be voltage (V+) output from the other end of the bridge circuits 410, and the second output voltage 620 is assumed to be voltage (V−) output from one end of the bridge circuits 410, the signal processor 420 may determine whether offset voltage occurs between the first and second output voltages 610 and 620 at an initial stage. The signal processor 420 may provide the additional current 430 to the bridge circuits 410 stepwise based on the clock (CLK). Then, it may again be determined whether offset voltage occurs between the first and second output voltages 610 and 620 according to the results of providing the additional current 430. As a result, the signal processor 420 may repeat the calibration process by stepwise providing the additional current 430 until offset voltage is removed.

Figure 22:
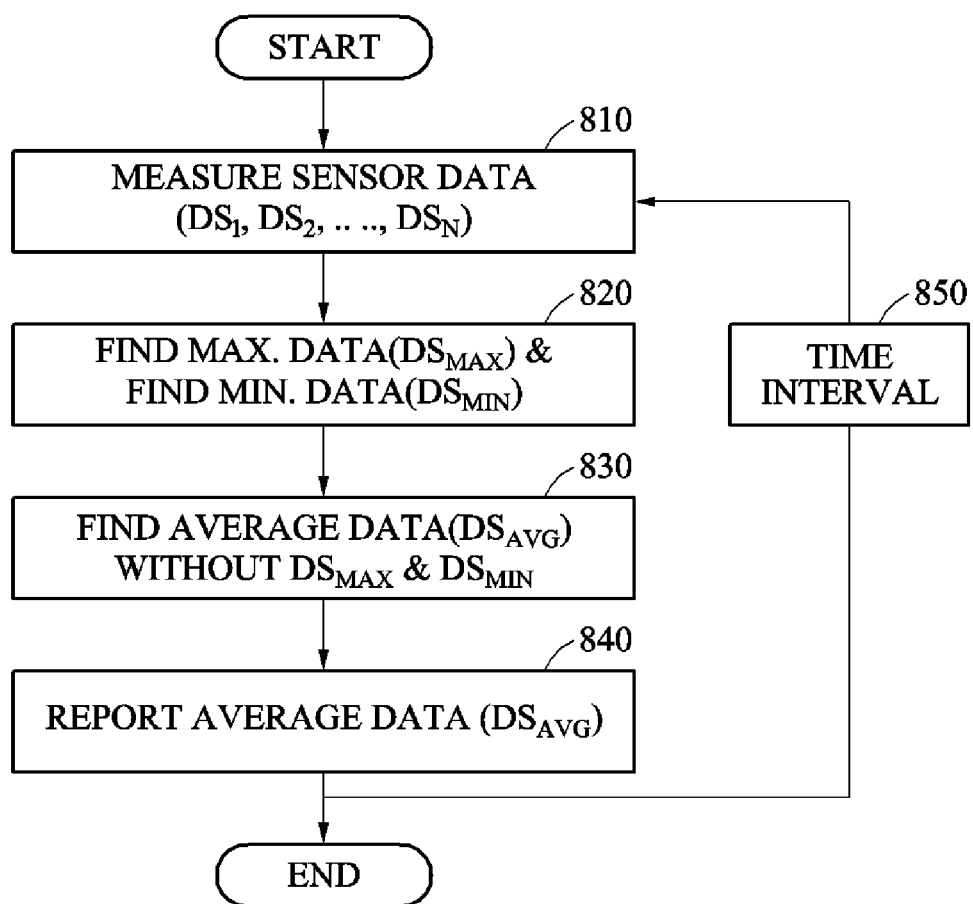
FIG. 22 is a flowchart showing that an average value of biological information is measured in a device for measuring biological information including a sensor array according to an embodiment of the present invention.

FIG. 22 is a flowchart showing that an average value of biological information is measured in a device for measuring biological information including a sensor array according to an embodiment of the present invention.

Referring to FIG. 22, a device for measuring biological information including a sensor array according to an embodiment of the present invention may measure resistance values ($DS_1$, $DS_2$, ..., $DS_N$) for an object using a plurality of sensors (Step 810).

In addition, a device for measuring biological information including a sensor array according to an embodiment of the present invention may calculate a maximum value ($DS_{MAX}$) and a minimum value ($DS_{MIN}$) of resistance values measured by a plurality of sensors (Step 820), and may calculate an average value of biological information ($DS_{AVG}$) for an object based on resistance values excluding the calculated maximum value ($DS_{MAX}$) and minimum value ($DS_{MIN}$) (Step 830).

Therefore, a device for measuring biological information including a sensor array according to an embodiment of the present invention may output the calculated average value of biological information ($DS_{AVG}$) (Step 840), and may repeat the process of calculating an average value of biological information for an object after a predetermined time interval has elapsed (Step 850).

Figure 23:
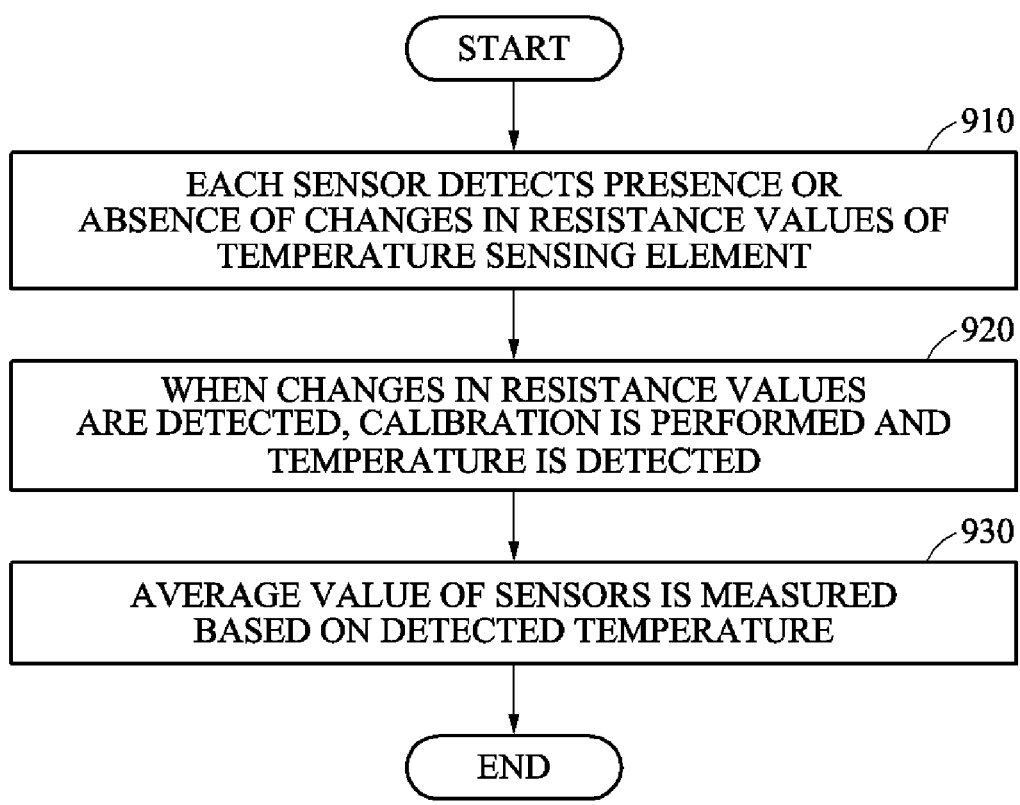
FIG. 23 is a flowchart showing a method of measuring biological information using a sensor array according to another embodiment of the present invention.

FIG. 23 is a flowchart showing a method of measuring biological information using a sensor array according to another embodiment of the present invention.

Referring to FIG. 23, each of a plurality of sensors may detect changes in the resistance values of a temperature sensing element (Step 910). More specifically, bridge circuits may detect changes in the resistance values of the temperature sensing element and provide the detected information to a signal processor.

When changes in the resistance values of the temperature sensing element are detected, the sensor array may perform calibration to minimize offset voltage generated according to changes in the resistance values of the temperature sensing element and may detect temperature (Step 920). More specifically, when changes in the resistance values of the temperature sensing element are detected, the controller may perform calibration to remove offset voltage included in the output voltage (V−, V+) of bridge circuits. The controller may repeat calibration by stepwise applying additional current until offset voltage is removed. The signal processor may sense temperature by processing the analog signals of the output voltage (V−, V+) of the bridge circuits from which offset voltage has been removed.

An average value measurement part may measure the average value of a plurality of sensors based on temperature sensed by the sensor array (Step 930). For example, the average value measurement part may measure an average value excluding specific ones of the sensors, and may improve the accuracy of biological information measurement.

Therefore, a device for measuring biological information including a sensor array according to another embodiment of the present invention may perform calibration by applying additional current to remove offset voltage generated according to changes in the resistance values of the temperature sensing element, and may improve the accuracy of biological information measurement by measuring an average value excluding specific ones of a plurality of sensors. In addition, a device for measuring biological information including a sensor array according to another embodiment of the present invention may determine the presence or absence of offset voltage according to changes in resistance values at every predetermined period, and may repeat calibration stepwise until offset voltage is removed.

The methods according to the embodiments of the present invention may be implemented in the form of a program command that can be executed through various computer means and recorded in a computer-readable medium. The computer-readable medium can store program commands, data files, data structures or combinations thereof. The program commands recorded in the medium may be specially designed and configured for the present invention or be known to those skilled in the field of computer software. Examples of a computer-readable recording medium include magnetic media such as hard disks, floppy disks and magnetic tapes, optical media such as CD-ROMs and DVDs, magneto-optical media such as floptical disks, or hardware devices such as ROMs, RAMs and flash memories, which are specially configured to store and execute program commands. Examples of the program commands include machine language code created by a compiler and high-level language code executable by a computer using an interpreter and the like. The hardware devices described above may be configured to operate as one or more software modules to perform the operations of the embodiments, and vice versa.

Although the present invention has been described through limited examples and figures, the present invention is not intended to be limited to the examples. Those skilled in the art will appreciate that various modifications, additions and substitutions are possible, without departing from the scope and spirit of the invention. For example, the described techniques may be performed in a different order than the described methods, and/or components of the described systems, structures, devices, circuits, etc., may be combined in a manner that is different from the described method, or appropriate results may be achieved even if replaced by other components or equivalents.

Therefore, other embodiments, other examples, and equivalents to the claims are within the scope of the following claims.

What is claimed is:

1. A device for measuring biological information, the device comprising:
    a sensor array formed on a substrate and comprising a plurality of sensors forming an island network in which nodes and a plurality of multi-channels are connected, wherein each of the plurality of sensors comprises terminals for measuring resistance values with respect to tissue activities and functions of skin tissues;
    an average value measurement part configured to measure an average value of biological information detected by the sensor array based on the resistance values measured by the terminals;
    a communication module configured to transmit the measured average value to the outside;
    a controller configured to control the average value measurement part to measure an average value of the biological information based on resistance values measured by at least one of the plurality of sensors in response to a control command received from the communication module; and
    a power supply for supplying driving power,
    wherein when a resistance value measured by the sensor array changes by a predetermined value or more, the controller is configured to apply additional current to the plurality of sensors so that the plurality of sensors perform calibration for minimizing offset voltage.

2. The device according to claim 1, wherein, in the sensor array, each of the plurality of sensors is configured to perform calibration to minimize offset voltage generated according to changes in resistance values of a temperature sensing element, and configured to measure resistance values for mapping the biological information.

3. The device according to claim 1, wherein, in each of the plurality of sensors, a plurality of multi-channels formed in a meander pattern is connected to the nodes and arranged in a matrix form on the substrate.

4. The device according to claim 1, wherein the multi-channels are thermistors.

5. The device according to claim 1, wherein each of the multi-channels has a length-to-width ratio of less than 100.

6. The device according to claim 1, wherein each of the multi-channels is formed at an angle of at least one of 0°, 90°, 45°, −45°, and −90° with respect to a horizontal direction to the substrate, so that change in the resistance values of the skin tissues is minimized.

7. The device according to claim 1, wherein the sensor array determines the presence or absence of offset voltage according to changes in resistance values of a temperature sensing element at every predetermined period, and repeats the calibration stepwise until the offset voltage is removed.

8. The device according to claim 1, wherein the average value measurement part measures an average value of remaining sensors except specific sensors among the plurality of sensors based on the measured resistance values.

9. The device according to claim 1, wherein, when the average value is measured by the average value measurement part, a sensor having highest or lowest temperature among the resistance values measured by the plurality of sensors is excluded.

10. The device according to claim 1, wherein, when the average value is measured by the average value measurement part, one or more sensors of the plurality of sensors which detects a sudden temperature change exceeding a predetermined reference is excluded.

11. The device according to claim 1, further comprising:
    a selection switch for selectively measuring resistance values of the plurality of sensors.

12. A method of measuring biological information using a sensor array, wherein the method uses a device for measuring biological information using a sensor array comprising a plurality of sensors forming a multi-channel connected island network, and the method comprises:
    a step of detecting the presence or absence of changes in resistance values of a temperature sensing element by each of the plurality of sensors;
    a step of detecting temperature by performing calibration to minimize offset voltage generated according to change in the resistance values when change in the resistance values is detected; and
    a step of measuring an average value of remaining sensors except specific sensors among the plurality of sensors based on the detected temperature,
    wherein the step of detecting the temperature comprises, when a resistance value measured by the sensor array changes by a predetermined value or more, a step of applying additional current to the plurality of sensors so that the plurality of sensors perform the calibration for minimizing the offset voltage.

* * * * *